(12) United States Patent
Krieg et al.

(10) Patent No.: US 12,173,351 B2
(45) Date of Patent: Dec. 24, 2024

(54) DNA-TAGGED METHANOL RESPONSIVE POLYMER FOR SINGLE-STRANDED NUCLEIC ACID PRODUCTION

(71) Applicants: Dana-Farber Cancer Institute, Inc., Boston, MA (US); President and Fellows of Harvard College, Cambridge, MA (US)

(72) Inventors: Elisha Krieg, Dresden (GB); William M. Shih, Cambridge, MA (US); Dionis Minev, Cambridge, MA (US); Richard Guerra, Milton, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 484 days.

(21) Appl. No.: 17/046,552

(22) PCT Filed: Apr. 11, 2019

(86) PCT No.: PCT/US2019/026867
§ 371 (c)(1),
(2) Date: Oct. 9, 2020

(87) PCT Pub. No.: WO2019/200026
PCT Pub. Date: Oct. 17, 2019

(65) Prior Publication Data
US 2021/0032683 A1    Feb. 4, 2021

Related U.S. Application Data

(60) Provisional application No. 62/656,546, filed on Apr. 12, 2018.

(51) Int. Cl.
C12Q 1/6806 (2018.01)
C12N 15/10 (2006.01)

(52) U.S. Cl.
CPC ....... *C12Q 1/6806* (2013.01); *C12N 15/1003* (2013.01); *C12Q 2523/101* (2013.01);
(Continued)

(58) Field of Classification Search
None
See application file for complete search history.

(56) References Cited

U.S. PATENT DOCUMENTS 9,085,802 B2 *  7/2015  Liu .................... C12Q 1/6806
2005/0009101 A1  1/2005  Blackburn
(Continued)

FOREIGN PATENT DOCUMENTS

WO   WO 1996/040901 A1   12/1996
WO   WO 2018/049315 A1   3/2018

OTHER PUBLICATIONS

Huang, et al. Pyrosequencing On-Chip Based on a Gel-Based Solid-Phase Amplification. Advances and Clinical Practice in Pyrosequencing, 289-300. (Year: 2016).*
(Continued)

*Primary Examiner* — Samuel C Woolwine
(74) *Attorney, Agent, or Firm* — Mueting Raasch Group

(57) ABSTRACT

Provided herein, in some embodiments, are methods and compositions for the production of long single-stranded DNA.

21 Claims, 21 Drawing Sheets

(52) U.S. Cl.
CPC .. *C12Q 2525/117* (2013.01); *C12Q 2525/131* (2013.01); *C12Q 2527/125* (2013.01); *C12Q 2531/113* (2013.01)

(56) References Cited

U.S. PATENT DOCUMENTS

2009/0277791 A1 11/2009 Vu et al.
2015/0299366 A1 10/2015 Zhang et al.
2020/0190505 A1 6/2020 Krieg et al.

OTHER PUBLICATIONS

Longo, et al. Use of uracil DNA glycosylase to control carry-over contamination in polymerase chain reactions. Gene 93:125-128. (Year: 1990).*

Maxam & Gilbert. A new method for sequencing DNA. Proc. Natl. Acad. Sci. USA 74(2):560-564. (Year: 1977).*

Kishi et al., Programmable autonomous synthesis of single-stranded DNA. Nat Chem. Feb. 2018;10(2):155-164. doi: 10.1038/nchem. 2872. Epub Nov. 6, 2017. PMID: 29359755; PMCID: PMC5784857.

Krieg et al., Selective Nascent Polymer Catch-and-Release Enables Scalable Isolation of Multi-Kilobase Single-Stranded DNA. Angew Chem Int Ed Engl. Jan. 15, 2018;57(3):714-718. doi: 10.1002/anie. 201710469. Epub Dec. 18, 2017. PMID: 29210156.

Minev et al., Rapid in vitro production of single-stranded DNA. Nucleic Acids Res. Dec. 16, 2019;47(22):11956-11962. doi: 10.1093/nar/gkz998. PMID: 31713635; PMCID: PMC7145709.

Praetorius et al., Biotechnological mass production of DNA origami. Nature. Dec. 6, 2017;552(7683):84-87. doi: 10.1038/nature24650. PMID: 29219963.

Beaucage et al., Deoxynucleoside phosphoramidites—A new class of key intermediates for deoxypolynucleotide synthesis. Tetrahedron Lett. 1981; 22:1859-62.

Beliveau et al., OligoMiner provides a rapid, flexible environment for the design of genome-scale oligonucleotide in situ hybridization probes. Proc Natl Acad Sci U S A. Mar. 6, 2018;115(10):E2183-E2192. doi: 10.1073/pnas.1714530115. Epub Feb. 20, 2018.

Beliveau et al., Versatile design and synthesis platform for visualizing genomes with Oligopaint FISH probes. Proc Natl Acad Sci U S A. Dec. 26, 2012; 109(52):21301-6. doi: 10.1073/pnas. 1213818110. Epub Dec. 11, 2012.

Buenemann et al., Synthesis and properties of acrylamide-substituted base pair specific dyes for deoxyribonucleic acid template mediated synthesis of dye polymers. Biochemistry. May 12, 1981;20(10):2864-74.

Chan et al., Capillary electrophoresis for capture and concentrating of target nucleic acids by affinity gels modified to contain single-stranded nucleic acid probes. Anal Chim Acta. Sep. 18, 2006;578(1):31-42. Epub May 27, 2006.

Chandra et al., DNA-catalyzed sequence-specific hydrolysis of DNA. Nat Chem Biol. Oct. 2009; 5(10):718-20. Author Manuscript, 7 pages. doi: 10.1038/nchembio.201. Epub Aug. 16, 2009.

Damase et al., Purification of single-stranded DNA by co-polymerization with acrylamide and electrophoresis. BioTechniques. Jun. 1, 2017; 62(6):275-282; DOI:10.2144/000114557.

Davis et al., Two Distinct Pathways Support Gene Correction by Single-Stranded Donors at DNA Nicks. Cell Rep. Nov. 8, 2016; 17(7):1872-1881. Author Manuscript, 22 pages. doi: 10.1016/j. celrep.2016.10.049.

Forster et al., Hydrophobically Modified Polyacrylamide Block Copolymers for 65 Fast, High-Resolution DNA Sequencing in Microfluidic Chips. Electrophoresis. Dec. 2008; 29(23):4669-4676. Author Manuscript, 14 pages.

Gu et al., Small, highly active DNAs that hydrolyze DNA. J Am Chem Soc. Jun. 19, 2013; 135(24):9121-9. Author Manuscript, 18 pages. doi: 10.1021/ja403585e. Epub Jun. 6, 2013.

Gyllensten et al., Generation of single-stranded DNA by the polymerase chain reaction and its application to direct sequencing of the HLA-DQA locus. Proc Natl Acad Sci U S A. Oct. 1988; 85(20):7652-6.

Kajua et al., Efficient preparation of single-stranded DNA for in vitro selection. Mol Biotechnol. Jun. 1997; 7(3):333-5.

Kenney et al., Mutation typing using electrophoresis and gel-immobilized Acrydite probes. Biotechniques. Sep. 1998; 25(3):516-21.

Kick et al., Efficient Production of Single-Stranded Phage DNA as Scaffolds for DNA Origami. Nano Lett. Jul. 8, 2015; 15(7):4672-6. doi: 10.1021/acs.nanolett.5b01461. Epub Jun. 3, 2015.

Kosuri et al., Large-scale de novo DNA synthesis: technologies and applications. Nat Methods. May 2014; 11(5):499-507. doi: 10.1038/nmeth.2918.

Krieg et al., A recyclable supramolecular membrane for size-selective separation of nanoparticles. Nat Nanotechnol. Mar. 2011; 6(3):141-6. doi: 10.1038/nnano.2010.274. Epub Jan. 23, 2011.

Li et al., Functional nucleic acid-based hydrogels for bioanalytical and biomedical applications. Chem Soc Rev. Mar. 7, 2016;45(5):1410-31. doi: 10.1039/c5cs00586h.

McHugh et al., Novel reagents for chemical cleavage at abasic sites and UV photoproducts in DNA. Nucleic Acids Res. May 25, 1995; 23(10):1664-70.

Paegel et al., Microchip bioprocessor for integrated anovolume sample purification and DNA sequencing. Anal Chem. Oct. 1, 2002;74(19):5092-8.

Palluck et al., De novo DNA synthesis using polymerase-nucleotide conjugates. Nat Biotechnol. Aug. 2018; 36(7):645-650. doi: 10.1038/nbt.4173. Epub Jun. 18, 2018.

Ponnuswamy et al., Oligolysine-based coating protects DNA nanostructures from low-salt denaturation and nuclease degradation. Nat Commun. May 31, 2017; 8:15654. doi: 10.1038/ncomms15654.

Pound et al., Polymerase chain reaction based scaffold preparation for the production of thin, branched DNA origami nanostructures of arbitrary sizes. Nano Lett. Dec. 2009; 9(12):4302-5. doi: 10.1021/n1902535q.

Rehman et al., Immobilization of acrylamide-modified oligonucleotides by co-polymerization. Nucleic Acids Res. Jan. 15, 1999; 27(2):649-55.

Richardson et al., Enhancing homology-directed genome editing by catalytically active and inactive CRISPR-Cas9 using asymmetric donor DNA. Nat Biotechnol. Mar. 2016; 34(3):339-44. doi: 10.1038/nbt.3481. Epub Jan. 20, 2016.

Roth et al., Reprogramming human T cell function and specificity with non-viral genome targeting. Nature. Jul. 2018; 559(7714):405-409. Author Manuscript, 41 pages. doi: 10.1038/s41586-018-0326-5. Epub Jul. 11, 2018.

Schindelin et al., Fiji: an open-source platform for biological-image analysis. Nat Methods. Jun. 28, 2012; 9(7):676-82. doi: 10.1038/nmeth.2019.

Schmidt et al., Scalable amplification of strand subsets from chip-synthesized oligonucleotide libraries. Nat Commun. Nov. 16, 2015;6:8634. doi: 10.1038/ncomms9634.

Seeman, N.C., An overview of structural DNA nanotechnology. Mol Biotechnol. Nov. 2007;37(3):246-57. Epub Jul. 12, 2007. Author Manuscript, 29 pages.

Svobodové et al., Comparison of different methods for generation of single-stranded DNA for SELEX processes. Anal Bioanal Chem. Aug. 2012; 404(3):835-42. doi: 10.1007/s00216-012-6183-4. Epub Jun. 26, 2012.

Tang et al., Polymerizing immobilization of acrylamide-modified nucleic acids and its application. Biosens Bioelectron. Mar. 15, 2009;24(7):1817-24. doi:10.1016/j.bios.2008.09.018. Epub Sep. 27, 2008.

Vasiliskov et al., Fabrication of microarray of gel-immobilized compounds on a chip by copolymerization. Biotechniques. Sep. 1999;27(3):592-4, 596-8, 600 passim.

Veneziano et al., Designer nanoscale DNA assemblies programmed from the top down. Science. Jun. 24, 2016; 352(6293):1534. Author Manuscript, 21 pages. doi: 10.1126/science.aaf4388. Epub May 26, 2016.

(56) References Cited

OTHER PUBLICATIONS

Veneziano et al., In vitro synthesis of gene-length single-stranded DNA. Sci Rep. Apr. 25, 2018; 8(1):6548. doi: 10.1038/s41598-018-24677-5.
Walker et al., Isothermal in vitro amplification of DNA by a restriction enzyme/DNA polymerase system. Proc Natl Acad Sci U S A. Jan. 1, 1992; 89(1):392-6.
Wei et al., Capture and release of protein by a reversible DNA-induced sol-gel transition system. Angew Chem Int Ed Engl. 2008; 47(2):331-3.
Xiao et al., Gel Immobilization of Acrylamide-Modified Single-Stranded DNA Template for Pyrosequencing. Advances in Clinical Practice in Pyrosequencing, Chapter 6. Springer Protocols Handbooks. Feb. 5, 2016.
Xiao et al., Gel immobilization of acrylamide-modified single-stranded DNA template for pyrosequencing. Electrophoresis. Jun. 2007;28(12):1903-12. doi: 10.1002/elps.200600794.
Xiong et al., Responsive DNA-based hydrogels and their applications. Macromol Rapid Commun. Aug. 2013;34(16):1271-83. Author Manuscript, 22 pages. doi: 10.1002/marc.201300411. Epub Jul. 16, 2013.
Amir et al., Universal computing by DNA origami robots in a living animal. Nat Nanotechnol. May 2014;9(5):353-357. doi: 10.1038/nnano.2014.58. Epub Apr. 6, 2014.
Andersen et al., Self-assembly of a nanoscale DNA box with a controllable lid. Nature. May 7, 2009;459(7243):73-6. doi: 10.1038/nature07971.
Bowman et al., Rapid production of single-stranded sequencing template from amplified DNA using magnetic beads. Methods Enzymol. 1993;224:399-406. doi: 10.1016/0076-6879(93)24030-x.
Chen et al., Self-Assembly of Large DNA Origami with Custom-Designed Scaffolds. ACS Appl Mater Interfaces. Jul. 25, 2018;10(29):24344-24348. doi: 10.1021/acsami.8b09222. Epub Jul. 12, 2018.
Dave et al., Regenerable DNA-functionalized hydrogels for ultrasensitive, instrument-free mercury(II) detection and removal in water. J Am Chem Soc. Sep. 15, 2010;132(36):12668-73. doi: 10.1021/ja106098j.
Douglas et al., A logic-gated nanorobot for targeted transport of molecular payloads. Science. Feb. 17, 2012;335(6070):831-4. doi: 10.1126/science.1214081.
Douglas et al., DNA-nanotube-induced alignment of membrane proteins for NMR structure determination. Proc Natl Acad Sci U S A. Apr. 17, 2007;104(16):6644-8. doi: 10.1073/pnas.0700930104. Epub Apr. 2, 2007.
Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.
Douglas et al., Self-assembly of DNA into nanoscale three-dimensional shapes. Nature. May 21, 2009;459(7245):414-8. doi: 10.1038/nature08016.
Fire et al., Rolling replication of short DNA circles. Proc Natl Acad Sci U S A. May 9, 1995;92(10):4641-5. doi: 10.1073/pnas.92.10.4641.
Hannon et al., Synthesis of PCR-derived, single-stranded DNA probes suitable for in situ hybridization. Anal Biochem. Aug. 1, 1993;212(2):421-7. doi: 10.1006/abio.1993.1350.
He et al., Aptamer based reversible DNA induced hydrogel system for molecular recognition and separation. Chem Commun (Camb). Sep. 14, 2010;46(34):6308-10. doi: 10.1039/c0cc01392g. Epub Jul. 30, 2010.
Hermanson, G. T. Bioconjugate Techniques, Third Edition. (Academic Press, 2013).
Joneja et al., Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
Kishi et al., SABER enables highly multiplexed and amplified detection of DNA and RNA in cells and tissues. BioRxiv. Aug. 27, 2018. doi.org/10.1101/401810.
Kuzyk et al., DNA-based self-assembly of chiral plasmonic nanostructures with tailored optical response. Nature. Mar. 14, 2012;483(7389):311-4. doi: 10.1038/nature10889.
Liedl et al., Controlled trapping and release of quantum dots in a DNA-switchable hydrogel. Small. Oct. 2007;3(10):1688-93. doi: 10.1002/smll.200700366.
Liu, Oligonucleotide-functionalized hydrogels as stimuli responsive materials and biosensors. Soft Matter. 2011. 7, 6757-6767. doi.org/10.1039/C1SM05284E.
Mitra et al., Fluorescent in situ sequencing on polymerase colonies. Anal Biochem. Sep. 1, 2003;320(1):55-65. doi: 10.1016/s0003-2697(03)00291-4.
Perrault et al., Virus-inspired membrane encapsulation of DNA nanostructures to achieve in vivo stability. ACS Nano. May 27, 2014;8(5):5132-40. doi: 10.1021/nn5011914. Epub Apr. 22, 2014.
Pinheiro et al., Challenges and opportunities for structural DNA nanotechnology. Nat Nanotechnol. Nov. 6, 2011; 6(12):763-72. doi: 10.1038/nnano.2011.187.
Rothemund, Folding DNA to create nanoscale shapes and patterns. Nature. Mar. 16, 2006;440(7082):297-302. doi: 10.1038/nature04586.
Zhang et al., Dynamic DNA nanotechnology using strand-displacement reactions. Nat Chem. Feb. 2011;3(2):103-13. doi: 10.1038/nchem.957.
Zhao et al., DNA origami delivery system for cancer therapy with tunable release properties. ACS Nano. Oct. 23, 2012;6(10):8684-91. doi: 10.1021/nn3022662. Epub Sep. 13, 2012.
Kujau, M.J., & Wölfl, S., "Efficient preparation of single-stranded DNA for in vitro selection," Jun. 1997, *Mol. Biotechnol.*, 7(3)333-35.

\* cited by examiner

DNA-TAGGED METHANOL RESPONSIVE POLYMER FOR SINGLE-STRANDED NUCLEIC ACID PRODUCTION

RELATED APPLICATIONS

This application is a national stage filing under 35 U.S.C. § 371 of international application number PCT/US2019/026867, filed Apr. 11, 2019, which was published under PCT Article 21(2) in English and claims the benefit under 35 U.S.C. § 119(e) of U.S. provisional application No. 62/656,546, filed Apr. 12, 2018, each of which is incorporated by reference herein in its entirety.

GOVERNMENT SUPPORT

This invention was made with government support under Grant No. 1435964 awarded by the National Science Foundation. The government has certain rights in the invention.

BACKGROUND

DNA is widely used as a programmable material in (bio)nanotechnology, with applications in diagnostics and therapeutics. Many of these applications demand highly pure, long single-stranded DNA (ssDNA). Commercially available long ssDNA with high purity and/or high yield, however, is expensive, while methods to produce and purify ssDNA often involve onerous protocols.

SUMMARY

Provided herein, in some aspects, are methods for producing single-stranded nucleic acids (e.g., ssDNA) that use a standard PCR with a DNA-tagged methanol-responsive polymer (MeRPy) (Krieg, E. et al. Angew. Chem. 2018; 57(3):714-718 and International Publication WO 2018/049315, each of which is incorporated herein by reference) as a forward primer. The tagged DNA sequence in the copolymer, in some embodiments, contains a deoxyuridine (dU) at the 3'-end of the sequence, enabling the selective recovery of both strands from the amplicon, via denaturing precipitation and the site-specific creation and cleavage of an abasic site (AB-site).

In some embodiments, the present disclosure provides a rapid, scalable, user-friendly method for in vitro production of high-purity ssDNA. In some embodiments, the ssDNA molecules range from 89-3315 nucleotides in length. In some embodiments, the ssDNA molecules are over 200 nucleotides (nt) in length. PCR with a forward primer bearing a methanol-responsive polymer generates a tagged amplicon that enables selective precipitation of the modified strand under denaturing conditions. Herein, it was demonstrated that the recovered ssDNA can be used, for example, for CRISPR/Cas9 homology-directed repair in human cells, DNA-origami folding, and fluorescent in situ hybridization.

Thus, some aspects of the present disclosure provide methods for producing single-stranded deoxyribonucleic acid (DNA), the method comprising: (a) amplifying a DNA template in a polymerase chain reaction mixture that comprises the DNA template, a pair of primers, at least one of which is tagged with a MeRPy (a MeRPy-tagged primer) and comprise a cleavage site, polymerase, and deoxynucleoside triphosphates to produce a double-stranded MeRPy-tagged amplicon; and (b) separating the double-stranded MeRPy-tagged amplicon into an untagged DNA strand and a MeRPy-tagged DNA strand comprising the cleavage site, and optionally isolating the untagged DNA strand.

It should be understood that the methods, in some embodiments, include the use of a pair of DNA primers—a forward primer and a reverse primer. Either primer (forward or reverse) may be tagged with MeRPy. In some embodiments, the forward primer is tagged with MeRPy. In other embodiments, the reverse primer is tagged with MeRPy. A DNA primer, generally, is a short sequence (e.g., 10 to 30 nucleotides) of DNA that binds to complementary sequence along a DNA strand (e.g., a DNA template). Thus, a PCR reaction herein include a pair of primers, one of which (the forward primer or the reverse primer) is tagged with MeRPy. In some embodiments, the forward primer is tagged with MeRPy while the reverse primer is untagged. In some embodiments, the reverse primer is tagged with MeRPy while the forward primer is untagged.

Also provided herein, in some aspects, are methods for producing single-stranded deoxyribonucleic acid (DNA), the method comprising: (a) copolymerizing a 5'-acrylamide-tagged single-strand DNA (ssDNA) primer with acrylamide monomers to produce a methanol-responsive polymer (MeRPy)-tagged primer, wherein the ssDNA primer comprises a cleavage site (e.g., a terminal cleavage site); (b) optionally purifying the MeRPy-tagged primer; (c) amplifying a DNA template in a polymerase chain reaction mixture that comprises the DNA template, a pair of primers, at least one of which is tagged with a MeRPy (a MeRPy-tagged primer), polymerase, and deoxynucleoside triphosphates to produce a double-stranded MeRPy-tagged amplicon; and (d) separating the double-stranded MeRPy-tagged amplicon into an untagged DNA strand and a MeRPy-tagged DNA strand comprising the cleavage site, and optionally isolating the untagged DNA strand.

In some embodiments, the methods further comprise cleaving the MeRPy-tagged DNA strand at the cleavage site to separate the MeRPy-tagged primer from the single-stranded DNA.

In some embodiments, the methods further comprise isolating the MeRPy-tagged primer and/or the single-stranded DNA.

In some embodiments, the cleavage site is a 3'-deoxyuridine (dU). In some embodiments, cleaving the MeRPy-tagged DNA strand comprises combining the MeRPy-tagged DNA strand with uracil-DNA glycosylase (UDG) to create an AB-site in the tagged DNA, and cleaving the AB-site with N,N'-Dimethylethylenediamine (DMEDA).

In some embodiments, purifying the DNA-tagged MeRPy comprises selective precipitation of the DNA-tagged MeRPy or electroelution of the DNA-tagged MeRPy.

In some embodiments, isolating the MeRPy-tagged primer comprises filtration, centrifugation, or selective precipitation of the MeRPy-tagged primer.

In some embodiments, the DNA template is a double-strand DNA template. In some embodiments, the DNA template is a single-strand DNA template. The DNA template may be circular or linear.

In some embodiments, a ssDNA primer has a length of 15 to 50 nucleotides, 15 to 40 nucleotide, 15 to 30 nucleotides, or 15 to 20 nucleotides. For example, the single-stranded oligonucleotides may have a length of 15, 20, 25, 30, 35, 40, 45, or 50 nucleotide.

In some embodiments, the DNA template has a length of 20 to 50,000 nucleotides, 20 to 25,000 nucleotides, 20 to 10,000 nucleotides, 20 to 1000 nucleotides, 20 to 100 nucleotides, 100 to 50,000 nucleotides, 100 to 25,000 nucleotides, 100 to 10,000 nucleotide, 100 to 1000 nucleotides, or 100 to 500 nucleotides. In some embodiments, the DNA template has a length of 20, 25, 50, 100, 200, 250, 500, 1000, 2000, 2500, 5000, or 10000 nucleotides.

In some embodiments, a single-stranded DNA has a length of 20 to 50,000 nucleotides, 20 to 25,000 nucleotides, 20 to 10,000 nucleotides, 20 to 1000 nucleotides, 20 to 100 nucleotides, 100 to 50,000 nucleotides, 100 to 25,000 nucleotides, 100 to 10,000 nucleotide, 100 to 1000 nucleotides, or 100 to 500 nucleotides. In some embodiments, the isolated single-stranded DNA has a length of 20, 25, 50, 100, 200, 250, 500, 1000, 2000, 2500, 5000, or 10000 nucleotides.

In some embodiments, a single-stranded DNA is greater than 200 nucleotides. In some embodiments, the isolated single-stranded DNA is 100, 150, 200, 250, 300, 350, 400, 450, 500, 550, 600, 650, 700, 750, 800, 850, 900, 950, 1000, 1500, 2000, 2500, 3000, 3500, 4500, 5000, 5500, 6000, 6500, 7000, 7500, 8000, 8500, 9000, 9500 or 10000 nucleotides in length.

In some embodiments, wherein separating the double-stranded MeRPy-tagged amplicon into an untagged DNA strand and a MeRPy-tagged DNA strand further comprises isolating the untagged DNA strand, optionally wherein the yield of isolated untagged strand is greater than 50%, greater than 60%, greater than 70%, greater than 80%, or greater than 90%. For example, the yield of the isolated untagged DNA strand may be 50%, 55%, 60%, 65%, 70%, 75%, 80%, 85%, 90%, or 95%. In some embodiments, the yield of the recovered untagged strand is 50% to 100%, 50% to 90%, 50% to 80%, 50% to 70%, 60% to 90%, 60% to 80%, or 60% to 70%.

In some embodiments, separating the double-stranded MeRPy-tagged amplicon into an untagged DNA strand and a MeRPy-tagged DNA strand further comprises isolating the MeRPy-tagged DNA strand, optionally wherein the yield of the isolated MeRPy-tagged DNA strand is greater than 50%, greater than 60%, or greater than 70%. For example, the yield of the recovered tagged strand may be 50%, 55%, 60%, 65%, or 70%. In some embodiments, the yield of the recovered tagged strand is 50% to 70% or 50% to 60%. In some embodiments, the yield of the isolated MeRPy-tagged DNA strand is 50% to 100%.

In some embodiments, the isolated single-stranded DNA is folded into a DNA nanostructure (e.g. for DNA origami). In some embodiments, the isolated single-stranded DNA may have a length of at least 2000 nucleotides, at least 3000 nucleotides, at least 4000 nucleotides, or at least 5000 nucleotides. In some embodiments, a single strand of DNA may have a length of 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3100, 3200, 3300, 3400, 3500, 3600, 3700, 3800, 3900, 4100, 4200, 4300, 4400, 4500, 4600, 4700, 4800, 4900, 5100, 5200, 5300, 5400, 5500, 5600, 5700, 5800, 5900, 6600, 6200, 6300, 6400, 6500, 6600, 6700, 6800, 6900, 7100, 7200, 7300, 7400, 7500, 7600, 7700, 7800, 7900, 8100, 8200, 8300, 8400, 8500, 8600, 8700, 8800, 8900, 9100, 9200, 9300, 9400, 9500, 9600, 9700, 9800, 9900, or 10000 nucleotides.

In some embodiments, the reverse primer or the single-stranded DNA comprises a fluorescent label (e.g., fluorophore, a dye, or a fluorescent molecule). A variety of fluorescent molecules can be used as labels including, for example, fluorescein and fluorescein derivatives, rhodamine and rhodamine derivatives, naphthylamine and naphthylamine derivatives, cyanine and cyanine derivatives, benzamidizoles, ethidiums, propidiums, anthracyclines, mith- ramycins, acridines, actinomycins, merocyanines, coumarins, pyrenes, chrysenes, stilbenes, anthracenes, naphthalenes, salicyclic acids, benz-2-oxa-1-diazoles (also called benzofurazans), fluorescamines and bodipy dyes. Other labels can be used and include, but are not limited to, chromophores, molecules that emit chemiluminescence, radioisotopes, electron dense particles, enzymes, cofactors, substrates for enzymes and ligands having specific binding partners (e.g., avidin/biotin).

BRIEF DESCRIPTION OF THE DRAWINGS

FIG. 3A is a schematic showing the final left-over target strand in a pellet (after decanting supernatant IV) dissolved in 100 µL water and heated to 95° C. for 5 minutes. Heating to 95° C. breaks AB-site and allows for control of left-over target strand in the pellet. FIG. 3B shows a denaturing PAGE analysis of dissolved final pellets after heating to 95° C. for 5 minutes.

FIG. 4A, from left to right, shows a schematic of the ligation of target ssDNA to DNA-tagged MeRPy. Native (not shown) and denaturing precipitation (supernatant I) removing impurities and splint strand. Creation and cleavage of AB-site releasing the target strand into the supernatant (supernatant II) after final separation step. FIG. 4B shows a denaturing PAGE analysis of target ssDNA ligation to DNA-tagged MeRPy and supernatants (I—denaturing, and II—native). Ligation of the target strand results in the depletion of the target band, trapped in the copolymer matrix and unable to migrate into the gel.

FIG. 5A shows the production of the polymer-tagged primer (MeRPy-tagged forward primer). A 5'-acrydite-modified primer including a dU is polymerized with acrylamide and sodium acrylate (ratio 99:1) to form a long linear DNA-tagged polymer. FIG. 5B shows a schematic of an example of a MeRPy-PCR procedure following standard PCR guidelines, including DNA-tagged MeRPy as a forward primer, a reverse primer, dsDNA template, dNTPs, and polymerase. FIG. 5C shows i. Recovery of strand 1 under alkaline denaturing conditions and methanol precipitation. ii. Recovery of strand 2, after treatment with UDG and DMEDA followed by a methanol precipitation. FIG. 5D shows the recovery yield for strands 1 and 2 of various lengths. Bar graphs denoting the recovery yield (%). Strand recovery yield was determined by the absolute recovered strand output (pmol) relative to MeRPy-PCR input (pmol). Data is shown as mean+/−STD (N=3). FIG. 5E shows gel electrophoresis of MeRPy-PCR derived ssDNA. Left, denaturing polyacrylamide gel with L—20 bp Ladder, C—200mer control from Integrated DNA Technologies (IDT). Middle and right, native agarose gels with L—1 kb Ladder, C—750mer control from IDT. MeRPy-PCR derived and commercial ssDNAs were loaded with normalized mass amounts for each gel lane in (FIG. 5E).

FIG. 6A shows genome editing in human cells using CRISPR/Cas9. (left) A genomically integrated GFP coding sequence is disrupted by the insertion of a stop codon and a 68-bp genomic fragment from the AAVS1 locus. Restoration of the GFP sequence by HDR with a ssDNA donor sequence results in GFP+ cells that can be quantified by FACS. (right) Bar graph depicting HDR efficiencies induced by MeRPy-PCR derived ssDNAs of different lengths vs. a 200mer chemically synthesized strand from IDT. Data is shown as mean+/−STD (N=3). FIG. 6B includes images from the generation of ssDNA scaffold via MeRPy-PCR from the phage genome, p'7308, and use in the folding of a 30 nm DNA origami barrel. Agarose gel electrophoresis (right) shows the purified scaffold strand (S) alongside the folded barrel structure (F). Transmission electron microscopy depicts the folded origami (left). Scale bars denote (left) 100 nm and (right) 50 nm. FIG. 6C shows a library comprising 42,000 probe sequences designed to tile along an 8.4 Mbp region of Human Chromosome 8 was amplified from a small amount of template using MeRPy-PCR with a Cy3-labeled reverse primer and subsequent recovery of fluor-tagged strand 1 library. The generated fluor-labeled ssDNA library was validated in situ on fixed human metaphase spreads and interphase cells. Scale bars denote 20 μm (zoom of metaphase spread scale bar denotes 5 μm).

DETAILED DESCRIPTION

The polymer-tagged primer of the present disclosure, surprisingly, is compatible with standard polymerase chain reaction (PCR) methods and can be used as a forward primer or a reverse primer to synthesize large quantities of long single-stranded DNA (ssDNA). A forward polymer-tagged primer as provided herein is referred to as a DNA-tagged methanol-responsive polymer (MeRPy). The data provided herein demonstrates that a synthesized MeRPy-tagged PCR product is compatible with enzymatic cleavage by uracil DNA glycosylase followed by DMEDA chemical cleavage to remove the tag (or other types of enzymatic cleavage), thereby producing a clean, single-stranded product. Compared to the ssDNA production methods described previously (see, e.g., International Publication WO 2018/049315), the methods provided herein are more convenient, accessible, and scalable. One advantage of the MeRPy-PCR of the present disclosure, compared to current methods, is that it uses, in some instances, standard PCR parameters to produce a tagged amplicon that enables selective precipitation of both DNA strands of a double-stranded product. In some embodiments, an acrydite-tagged oligonucleotide is polymerized and used as a forward primer in a PCR. In other embodiments, only one DNA-tagged MeRPy species is made, and a new forward primer is simply be ligated onto the tagged sequence.

Figure 1A:
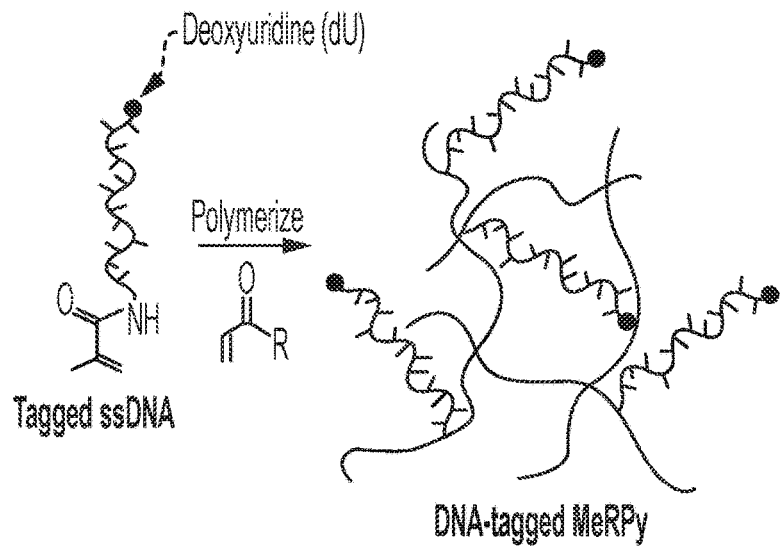
FIG. 1A shows a schematic of an example of a DNA-tagged methanol-responsive polymer (MeRPy) production method.
Figure 1B:
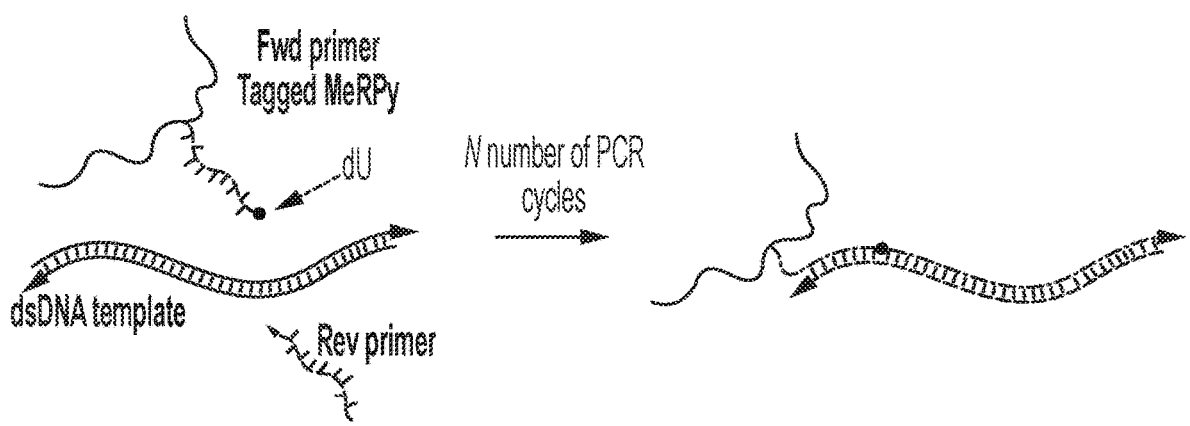
FIG. 1B shows a schematic of an example of a MeRPy-PCR.
Figure 1C:
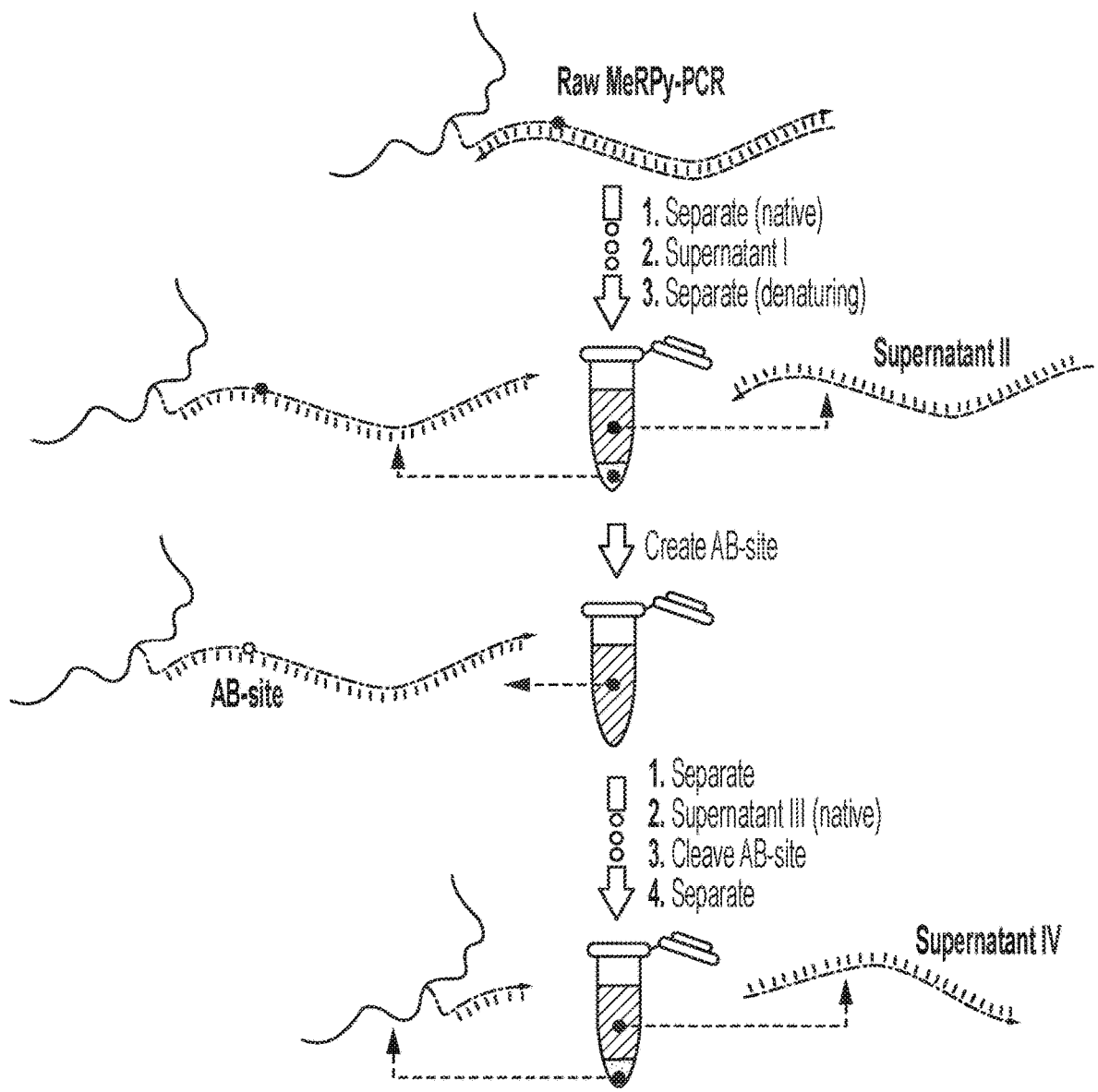
FIG. 1C shows a schematic of single-stranded DNA (ssDNA) separation and retrieval following a MeRPy-PCR.

An example ssDNA production method is provided in FIGS. 1A-1C. Acrylamide-tagged ssDNA (containing a deoxyuridine (dU) on the 3'-end of the sequence, or anywhere within the primer sequence) is copolymerized with acrylamide monomers, resulting in linear copolymers with high molecular weight (FIG. 1A), which are referred to herein as a DNA-tagged methanol responsive polymers (DNA-tagged MeRPys). Following this sequestration step, an optional purification step may be performed. For example, unreacted ssDNA, acrylamide monomers, and other reagents can be removed from the mixture by selective precipitation of the copolymer or by electroelution. Next, a standard PCR is performed with the DNA-tagged MeRPy. The DNA-tagged MeRPy is used as a forward primer (thus, includes a sequence that binds to a template of interest) in a standard PCR to produce MeRPy-tagged amplicons (FIG. 1B). Alternatively, a forward primer sequence (e.g. random forward primer sequence) (that includes a sequence that binds to a template of interest) may be added (e.g., ligated) to the DNA-tagged MeRPy sequence (see Examples section). Following the PCR, the double-stranded DNA amplicons are dehybridized under denaturing conditions and the complementary untagged strand can be recovered (FIG. 1C). Recovery of the tagged strand may include creating an abasic site (AB-site) in the tagged strand. This may be achieved by treatment with uracil-DNA glycosylase (UDG) to create an AB-site from the dU 3'-end of the DNA sequence tagged into MeRPy (FIG. 1C). Treatment with N,N'-Dimethylethylenediamine (DMEDA) cleaves the AB-site and liberates the ssDNA (FIG. 1C). Finally, the DNA-tagged MeRPy is removed from the released ssDNA by filtration, centrifugation, or selective precipitation, for example (FIG. 1C).

Methods that can be used to add the forward primer sequence to the DNA-tagged MeRPy sequence include, but are not limited to ligation, chemical ligation, click chemistry, click ligation (e.g. by copper-catalyzed azide-alkyne (CuAAC) reaction), and linkers. As used herein, the term "ligation" refers to covalent attachment of two nucleic acid sequences to make a contiguous sequence. Any method to covalently link nucleic acid sequences is contemplated for adding the forward primer to the DNA-tagged MeRPy sequence. In some embodiments, ligation of the forward primer is done by a ligase (e.g. DNA ligase). Multiple ligases, each having characterized reaction conditions, are known in the art, and include, without limitation NAD+-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof.

Sequestration

An initial step of a method, as provide herein, includes sequestration in solution of acrylamide monomers and acrylamide-tagged (e.g., 5'-acrylamide-tagged) single-stranded oligonucleotides to form a DNA-tagged methanol-responsive polymer (MeRPy). Acrylamide copolymerization, which produces polyacrylamide (PAA), is robust, has virtually unlimited loading capacity and does not require high purity of the precursor. Further, PAA is a biocompatible polymer with low nonspecific binding to DNA and other biomacromolecules. Thus, PAA is an ideal sequestration material, as it exhibits weak nonspecific binding, even for long DNA strands. When acrylamide monomers are combined with acrylamide-tagged single-stranded oligonucleotides in solution, for example, in a solution comprising ammonium persulfate and tetramethylethylenediamine, a linear copolymer of polyacrylamide containing single-stranded oligonucleotide is formed. With the addition of a crosslinking agent, such as bisacrylamide (BAA), a high molecular weight crosslinked copolymer is formed (the linear copolymer strands are crosslinked to each other in the presence of a crosslinking agent).

An acrylamide-tagged oligonucleotide may be single-stranded (ss) or double-stranded (ds). The acrylamide-tagged oligonucleotide may comprise DNA, RNA or a hybrid molecule, for example, where the oligonucleotide contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine. In some embodiments, the acrylamide-tagged oligonucleotide is DNA.

An acrylamide-tagged oligonucleotide of the present disclosure may include backbone modifications, base modifications, and/or sugar modifications. Examples of these modifications are known. In some embodiments, an acrylamide-tagged oligonucleotides comprise a backbone other than a phosphodiester backbone. For example, an acrylamide-tagged oligonucleotide, in some embodiments, may comprise phosphoramide, phosphorothioate, phosphorodithioate, O-methylphophoroamidite linkages, peptide nucleic acids or a combination of any two or more of the foregoing linkages. The acrylamide-tagged oligonucleotides of the present disclosure, in some embodiments, have a homogenous backbone (e.g., entirely phosphodiester or entirely phosphorothioate) or a heterogeneous (or chimeric) backbone. Phosphorothioate backbone modifications may render an oligonucleotides less susceptible to nucleases and thus more stable (as compared to a native phosphodiester backbone nucleic acid) under certain conditions. Other linkages that may provide more stability to an acrylamide-tagged oligonucleotide of the present disclosure include, but are not limited to, phosphorodithioate linkages, methylphosphonate linkages, methylphosphorothioate linkages, boranophosphonate linkages, peptide linkages, alkyl linkages and dephospho-type linkages.

In some embodiments, an acrylamide-tagged oligonucleotide further comprises one or more additional oligonucleotide(s), for example, to generate a single batch of acrylamide-tagged oligonucleotides. With this single batch, a new sequence may be ligated or added via "click" chemistry, thus eliminating successive rounds of polymerization any time a new sequence is used.

Acrylamide monomers (e.g., $C_3H_5NO$) are commercially available and are typically used to produce copolymers of polyacrylamide. The concentration of acrylamide monomers in a solution may be, for example, 5-500 mg/ml (0.5-50 wt %). In some embodiments, the concentration of acrylamide monomers in a solution is 10-500 mg/ml, 10-450 mg/ml, 10-400 mg/ml, 10-350 mg/ml, 10-300 mg/ml, 10-250 mg/ml, 10-200 mg/ml, 10-150 mg/ml, 10-100 mg/ml, 10-50 mg/ml, 10-25 mg/ml, 5-500 mg/ml, 5-450 mg/ml, 5-400 mg/ml, 5-350 mg/ml, 5-300 mg/ml, 5-250 mg/ml, 5-200 mg/ml, 5-150 mg/ml, 5-100 mg/ml, 5-50 mg/ml, 5-25 mg/ml or 5-10 mg/ml. For example, the concentration of acrylamide monomers in a solution may be 5, 10, 15, 20, 25, 30, 35, 40, 45, 50, 55, 60, 65, 70, 75, 80, 85, 90, 95, 100, 125, 150, 175, 200, 250, 300, 350, 400, 450 or 500 mg/ml of the solution.

In some embodiments, the concentration of acrylamide monomers in a solution is 1-50 wt %, 1-45 wt %, 1-40 wt %, 1-35 wt %, 1-30 wt %, 1-25 wt %, 1-20 wt %, 1-15 wt %, 1-10 wt %, 1-5 wt %, 1-2.5 wt %, 0.5-50 wt %, 0.5-45 wt %, 0.5-40 wt %, 0.5-35 wt %, 0.5-30 wt %, 0.5-25 wt %, 0.5-20 wt %, 0.5-15 wt %, 0.5-10 wt %, 0.5-5 wt %, 0.5-2.5 wt % or 0.5-1 wt %. For example, the concentration of acrylamide monomers in a solution may be 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 12.5, 15.0, 17.5, 20.0, 25.0, 30.0, 35.0, 40.0, 45.0 or 50.0 wt % of the solution.

In some embodiments, the concentration of acrylamide monomers in solution for the production of a linear copolymer (LC) is 40-60 mg/ml (e.g., 50 mg/ml) (or 4-6 wt %). In some embodiments, the concentration of acrylamide monomers in solution for the production of a high molecular weight crosslinked copolymer (HMWCC) is 10-15 mg/ml (e.g., 12.5 mg/ml) (or 1-1.5 wt %).

The concentration of acrylamide-tagged single-stranded oligonucleotides in a solution may be, for example, 0.01-10 mg/ml of the solution. In some embodiments, the acrylamide-tagged single-stranded oligonucleotide concentration is 0.01-10 mg/ml, 0.01-9 mg/ml, 0.01-8 mg/ml, 0.01-7 mg/ml, 0.01-6 mg/ml, 0.01-5 mg/ml, 0.01-4 mg/ml, 0.01-3 mg/ml, 0.01-2 mg/ml, 0.01-1 mg/ml. In some embodiments, the acrylamide-tagged single-stranded oligonucleotide concentration is 0.1-10 mg/ml, 0.1-9 mg/ml, 0.1-8 mg/ml, 0.1-7 mg/ml, 0.1-6 mg/ml, 0.1-5 mg/ml, 0.1-4 mg/ml, 0.1-3 mg/ml, 0.1-2 mg/ml, 0.1-1 mg/ml, 0.2-10 mg/ml, 0.2-9 mg/ml, 0.2-8 mg/ml, 0.2-7 mg/ml, 0.2-6 mg/ml, 0.2-5 mg/ml, 0.2-4 mg/ml, 0.2-3 mg/ml, 0.2-2 mg/ml, 0.2-1 mg/ml, 0.3-10 mg/ml, 0.3-9 mg/ml, 0.3-8 mg/ml, 0.3-7 mg/ml, 0.3-6 mg/ml, 0.3-5 mg/ml, 0.3-4 mg/ml, 0.3-3 mg/ml, 0.3-2 mg/ml, 0.3-1 mg/ml, 0.4-10 mg/ml, 0.4-9 mg/ml, 0.4-8 mg/ml, 0.4-7 mg/ml, 0.4-6 mg/ml, 0.4-5 mg/ml, 0.4-4 mg/ml, 0.4-3 mg/ml, 0.4-2 mg/ml, 0.4-1 mg/ml, 0.5-10 mg/ml, 0.5-9 mg/ml, 0.5-8 mg/ml, 0.5-7 mg/ml, 0.5-6 mg/ml, 0.5-5 mg/ml, 0.5-4 mg/ml, 0.5-3 mg/ml, 0.5-2 mg/ml, 0.5-1 mg/ml, 0.6-10 mg/ml, 0.6-9 mg/ml, 0.6-8 mg/ml, 0.6-7 mg/ml, 0.6-6 mg/ml, 0.6-5 mg/ml, 0.6-4 mg/ml, 0.6-3 mg/ml, 0.6-2 mg/ml, 0.6-1 mg/ml, 0.7-10 mg/ml, 0.7-9 mg/ml, 0.7-8 mg/ml, 0.7-7 mg/ml, 0.7-6 mg/ml, 0.7-5 mg/ml, 0.7-4 mg/ml, 0.7-3 mg/ml, 0.7-2 mg/ml, 0.7-1 mg/ml, 0.8-10 mg/ml, 0.8-9 mg/ml, 0.8-8 mg/ml, 0.8-7 mg/ml, 0.8-6 mg/ml, 0.8-5 mg/ml, 0.8-4 mg/ml, 0.8-3 mg/ml, 0.8-2 mg/ml, or 0.8-1 mg/ml, of the solution. In some embodiments, the concentration of acrylamide-tagged single-stranded oligonucleotide is 1-5 mg/ml, 1-4 mg/ml, 1-3 mg/ml, or 1-2 mg/ml of the solution. In some embodiments, the acrylamide-tagged single-stranded oligonucleotide concentration is 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml or 10 mg/ml of the solution.

The methods and compositions of the present disclosure are particularly useful for the production of long ssDNA (although the methods and compositions may also be used for producing shorter ssDNA, e.g., less than 100 nucleotide base pairs), which is produced from a long DNA template. Thus, the length of a template, and/or a tagged and/or untagged PCR amplicon in a solution, in some embodiments, is at least 100 nucleotide base pairs (bp). For example, the length may be 100-1000 bp, 100-5000 bp, 100-10000 bp, 100-25000 bp, or 100-50000 bp. In some embodiments, the length is 1000-50000 bp, 1000-25000 bp, 1000-10000 bp, 1000-5000 bp, or 1000-2000 bp. In some embodiments, the length is 100, 200, 300, 400, 500, 600, 700, 800, 900, 1000, 1500, 2000, 2500, 3000, 3500, 4500, 5000, 5500, 6000, 6500, 7000, 7500, 8000, 8500, 9000, 9500 or 10000 bp. In some embodiments, the length is greater than 50000 bp, or shorter than 100 bp. In some embodiments, the length is 10-100 bp.

A sequestration solution may also comprise a reagent that initiates copolymer formation. For example, a sequestration solution may comprise ammonium persulfate (APS), tetramethylethylenediamine (TEMED), or a combination of APS and TEMED to catalyze the polymerization of acrylamide to form a polyacrylamide copolymer. Other similar reagents are encompassed by the present disclosure, including, but not limited to: riboflavin and TEMED; riboflavin, APS and TEMED; APS and metabisulfite; APS, nitrotris(propionamide), and sodium sulfate; or APS and ammonium ferrous sulfate.

The concentration of APS and TEMED in a sequestration solution may vary between 0.0005 wt % and 0.2 wt %, for example, depending in part on the intended copolymer and on the presence (or absence) or oxygen. For sequestration of acrylamide-tagged single-stranded oligonucleotides to form a linear copolymer (LC) protected from oxygen, the APS concentration may be 0.01 wt %-0.1 wt %. In some embodiments, the APS concentration is 0.01 wt %, 0.02 wt %, 0.03 wt %, 0.04 wt %, 0.05 wt %, 0.06 wt %, 0.07 wt %, 0.08 wt %, 0.09 wt %, or 0.10 wt %. In some embodiments, the APS concentration is 0.05 wt %. Likewise, for sequestration of acrylamide-tagged single-stranded oligonucleotides to form a LC protected from oxygen, the TEMED concentration may be 0.01 wt %-0.1 wt %. In some embodiments, the TEMED concentration is 0.01 wt %, 0.02 wt %, 0.03 wt %, 0.04 wt %, 0.05 wt %, 0.06 wt %, 0.07 wt %, 0.08 wt %, 0.09 wt %, or 0.10 wt %. In some embodiments, the TEMED concentration is 0.05 wt %.

For sequestration of acrylamide-tagged single-stranded oligonucleotides to form a high molecular weight cross-linked copolymer (HMWCC) protected from oxygen, the APS concentration may be 0.01 wt %-0.1 wt %. In some embodiments, the APS concentration is 0.01 wt %, 0.02 wt %, 0.03 wt %, 0.04 wt %, 0.05 wt %, 0.06 wt %, 0.07 wt %, 0.08 wt %, 0.09 wt %, or 0.10 wt %. In some embodiments, the APS concentration is 0.05 wt %. Likewise, for sequestration of acrylamide-tagged single-stranded oligonucleotides to form a HMWCC protected from oxygen, the TEMED concentration may be 0.01 wt %-0.1 wt %. In some embodiments, the TEMED concentration is 0.01 wt %, 0.02 wt %, 0.03 wt %, 0.04 wt %, 0.05 wt %, 0.06 wt %, 0.07 wt %, 0.08 wt %, 0.09 wt %, or 0.10 wt %. In some embodiments, the TEMED concentration is 0.05 wt %.

In the presence of oxygen concentrations of APS and TEMED may be 0.05 wt %-0.2% wt %. For example, the APS and/or the TEMED concentration in the presence of oxygen may be 0.05 wt %, 0.06 wt %, 0.07 wt %, 0.08 wt %, 0.09 wt %, 0.10 wt %, 0.11 wt %, 0.12 wt %, 0.13 wt %, 0.14 wt %, 0.15 wt %, 0.16 wt %, 0.17 wt %, 0.18 wt %, 0.19 wt % or 0.20 wt %.

Various crosslinking agents may be added to a sequestration solution to produce crosslinked copolymer. In some embodiments, the crosslinking reagent comprises bisacrylamide (BAA). In some embodiments, the crosslinking reagent comprises N,N'-methylenebisacrylamide (or $C_7H_{10}N_2O_2$). In some embodiments, the crosslinking reagent comprises piperazine diacrylamide, N,N'(hexamethylenebis(methacrylamide), N,N'-ethylenebis(acrylamide) or combinations thereof.

A sequestration solution may comprises a AA:BAA ratio of greater than 1:1. In some embodiments, a AA:BAA ratio is 1:1 to 200:1. For example, a AA:BAA ratio may be 200:1, 190:1, 180:1, 170:1, 160:1, 150:1, 140:1, 130:1, 120:1, 120:1, 100:1, 90:1, 80:1, 70:1, 60:1, 50:1, 40:1, 30:1, 20:1, 10:1, 9:1, 8:1, 7:1, 6:1, 5:1, 4:1, 3:1, 2:1 or 1:1. In some embodiments, a ratio of AA:BAA is greater than 200:1.

Copolymer-linked dsDNA, as described above, may be produced by combining acrylamide monomers and acrylamide-tagged single-stranded oligonucleotides in a sequestration solution. One of two different copolymers may be produced depending on the presence or absence of a crosslinking agent. In general, a "copolymer-linked dsDNA" refers to a composition comprising acrylamide linked to (attached to) acrylamide-tagged dsDNA. In the absence of a crosslinking agent, and, in some embodiments, in the presence of acrylate, a linear polymer containing acrylamide-acrylamide bonds as well as sequestered single-stranded oligonucleotides is formed, which is referred to as a "linear copolymer (LC)." In the presence of a crosslinking agent (and by varying the concentration of reagents that initiate copolymer formation), the linear copolymers are crosslinked to each other and a "high molecular weight crosslinked copolymer (HMWCC)" is formed. A HMWCC may have a molecular weight of, for example, at least 1 kDa (kilodaltons), at least 10 kDa, at least 100 kDa or at least 1000 kDa.

A copolymer may comprise, for example, acrylamide, bisacrylamide, acrylate, sodium acrylate, or other acrylic monomers. In some embodiments, a copolymer comprises acrylamide and acrylate. In other embodiments, a copolymer comprises acrylamide and bisacrylamide.

A linear copolymer, in some embodiments, is produced using a solution of acrylamide and acrylate. The ratio of acrylamide to acrylate may be 50:1 to 200:1. For example, the ratio of acrylamide to acrylate in solution may be 50:1, 60:1, 70:1, 80:1, 90:1, 100:1, 110:1, 120:1, 130:1, 140:1, 150:1, 160:1, 170:1, 180:1, 190:1 or 200:1. In some embodiments, the ratio of acrylamide to acrylate is 91:1, 92:1, 93:1, 94:1, 95:1, 96:1, 97:1, 98:1, 99:1, 100:1, 101:1, 102:1, 103:1, 104:1 or 105:1. In some embodiments, the ratio of acrylamide to acrylate is at least 99:1. In some embodiments, the ratio of acrylamide to acrylate is 99:1. In some embodiments, nitrogen is added to the solution to remove oxygen. Additional components such as TEMED and 10% APS may be used, for example, to achieve polymerization.

Advantageously, the methods provided herein produce copolymers that comprise a high percentage of the dsDNA starting material. In some embodiments, a copolymer-linked dsDNA may comprise at least 80% of the acrylamide-tagged single-stranded oligonucleotides from a sequestration solution (at least 80% of the acrylamide-tagged dsDNA starting material). For example, a copolymer-linked single-stranded oligonucleotides may comprise at least 85%, at least 90%, or at least 95% of the acrylamide-tagged single-stranded oligonucleotides from a sequestration solution. In some embodiments, a copolymer-linked single-stranded oligonucleotides may comprises 50-90%, 55-90%, 60-90%, 65-90%, 70-90%, 75-90%, 80-90%, 85-90%, 50-95%, 55-95%, 60-95%, 65-95%, 70-95%, 75-95%, 80-95%, 85-95%, 50-100%, 55-100%, 60-100%, 65-100%, 70-100%, 75-100%, 80-100%, 85-100%, 90-100%, or 95-100% of the acrylamide-tagged single-stranded oligonucleotides from a sequestration solution.

A sequestration reaction may be performed "under conditions that result in formation of a copolymer containing single-stranded oligonucleotides." It should be understood that such conditions are described throughout the present disclosure and take into account the type and concentration of the disclosed reagents as well as incubation times and temperatures.

Thus, a sequestration solution may be incubated at room temperature, for example, for 1-48 hours. In some embodiments, a sequestration solution is incubated for 1-6 hours, 1-8 hours, 1-12 hours, 1-24 hours, 1-36 hours, or 1-48 hours. Incubation time may depend on the type of intended copolymer. For example, production of a linear copolymer may only require an incubation time of 2 hours or less. Thus, in some embodiments, a sequestration solution (e.g., without crosslinking agent) is incubated for 30 min, 1 hour, 1.5 hours, 2 hours or 2.5 hours. In some embodiments, a sequestration solution without crosslinking agent is incubated for 30 min-2.5 hours. In some embodiments, a sequestration solution without crosslinking agent is incubated for about 2 hours. For production of a crosslinked copolymer, the incubation time may be longer than 2 hours, for example, as long as 8 hours, or longer. Thus, in some embodiments, a sequestration solution (e.g., with crosslinking agent) is incubated for (or for at least) 6, 7, 8, 9, 10, 11, or 12 hours. In some embodiments, a sequestration solution with crosslinking agent is incubated for 6-12 hours. In some embodiments, a sequestration solution with crosslinking agent is incubated for about 8 hours.

Purification

In some instances, it may be advantageous to purify a DNA-tagged MeRPy (separate a DNA-tagged MeRPy from contaminants, such as unreacted acrylamide monomers) following sequestration of acrylamide-linked single-stranded oligonucleotides. Thus, in some embodiments a DNA-tagged MeRPy is purified following sequestration and prior to the PCR. In some embodiments, methanol is used to selectively precipitate copolymer-linked single-stranded oligonucleotides. For example, the addition of methanol having of volume of at least 2x (e.g., 2x, 2.5x, 3x, 3.5x, 4x, 4.5x, 5x) relative to the total volume of the sequestration solution results in selective precipitation of the DNA-tagged MeRPy species. Thus, in some embodiments, methods of the present disclosure comprise adding to a sequestration solution at least 2 volumes of methanol. In some embodiments, methods of the present disclosure comprise adding to a sequestration solution at least 3 volumes of methanol. The precipitate is then collected from solution and reconstituted in an aqueous buffer, for example. This solution of buffer and purified DNA-tagged MeRPy may then be subjected to standard PCR, as described below.

Alternatively, a DNA-tagged MeRPy may be purified by conventional electroelution methods, whereby the sequestration solution is loaded a substrate, such as into the well of a gel (e.g., agarose gel), into electrolyte solution, onto a membrane, or into an electroelution chamber, and an electric current is applied to the substrate to elute contaminants into the substrate, for example.

As indicated above, this purification process (between sequestration and PCR) is optional. A method of producing ssDNA, for example, may proceed from a sequestration step(s) directly to the PCR step(s), discussed below.

Standard Polymerase Chain Reaction for the Production of ssDNA

As indicated above, the DNA-tagged MeRPy may be used as a forward primer in a standard PCR to produce a double-stranded amplicon, which may then be denatured for subsequent single-stranded DNA purification. Standard PCR conditions are well-known, and Standard PCR conditions (for New England Biolab®'s (NEB's) Standard Taq polymerase) include the following general steps:

Example Thermocycling Conditions for a Standard PCR:

| STEP | TEMP | TIME |
| --- | --- | --- |
| Initial Denaturation | 95° C. | 30 seconds |
| 30 Cycles | 95° C. | 15-30 seconds |
|  | 45-68° C. | 15-60 seconds |
|  | 68° C. | 1 minute/kb |
| Final Extension | 68° C. | 5 minutes |
| Hold | 4-10° C. |  |

Example Reaction Components for a Standard PCR:

| Component | 25 µl reaction | 50 µl reaction | Final Concentration |
| --- | --- | --- | --- |
| 10× Standard Reaction Buffer | 2.5 µl | 5 µl | 1× |
| 10 mM dNTPs | 0.5 µl | 1 µl | 200 µM |
| 10 µM Forward Primer | 0.5 µl | 1 µl | 0.2 µM (0.05-1 µM) |
| 10 µM Reverse Primer | 0.5 µl | 1 µl | 0.2 µM (0.05-1 µM) |
| Template DNA | variable | variable | <1,000 ng |
| DNA Polymerase (e.g., Taq) | 0.125 µl | 0.25 µl | 1.25 units/50 µl PCR |
| Nuclease-free water | to 25 µl | to 50 µl |  |

The following general PCR guidelines may be used:

Template: use of high quality, purified DNA templates enhances the success of PCR. The amounts of DNA template for a 50 µl reaction may be as follows: genomic DNA, 1 ng-1 µg; plasmid or viral, 1 pg-1 ng.

Primers: oligonucleotide primers are generally 20-40 nucleotides in length and can have a GC content of 40-60%. Computer programs such as Primer3 can be used to design or analyze primers. The final concentration of each primer in a reaction may be 0.05-1 µM, typically 0.1-0.5 µM.

MC and additives: $Mg^+$ concentration of 1.5-2.0 mM is optimal for most PCR products generated with DNA Polymerase. The final $Mg^{++}$ concentration in 1× Standard Reaction Buffer is 1.5 mM. This supports satisfactory amplification of most amplicons. $Mg^{++}$ can be further optimized in 0.5 or 1.0 mM increments using $MgCl_2$. Amplification of some difficult targets, like GC-rich sequences, may be improved with additives, such as DMSO or formamide.

Deoxynucleotides: the final concentration of dNTPs is typically 200 µM of each deoxynucleotide.

DNA Polymerase Concentration: DNA polymerase may be used at a concentration of 25 units/ml (1.25 units/50 µl reaction). The optimal concentration of DNA Polymerase may range from 5-50 units/ml (0.25-2.5 units/50 µl reaction) in some embodiments.

Denaturation: an initial denaturation of 30 seconds at 95° C. is sufficient for most amplicons from pure DNA templates. For difficult templates such as GC-rich sequences, a longer initial denaturation of 2-4 minutes at 95° C. may be used prior to PCR cycling to fully denature the template. With colony PCR, an initial 5 minute denaturation at 95° C. is recommended. During thermocycling a 15-30 second denaturation at 95° C. may be used, for example.

Annealing: the annealing step may be 15-60 seconds, for example. Annealing temperature is based on the $T_m$ of the primer pair and is typically 45-68° C. Annealing temperatures can be optimized by doing a temperature gradient PCR starting 5° C. below the calculated $T_m$. Tm Calculators are publicly available. When primers with annealing temperatures above 65° C. are used, a 2-step PCR protocol may be used.

Extension: the extension temperature may be 68° C., for example. Extension times are generally 1 minute per kb. A final extension of 5 minutes at 68° C. may be used, for example.

Cycle number: generally, 25-35 cycles yields sufficient product. Up to 45 cycles may be required to detect low-copy-number targets, in some embodiments.

Dehybridization

Following PCR, the resulting double-stranded MeRPy-tagged amplicon (MeRPy-tagged DNA) may be denatured to separate untagged ssDNA from the tagged ssDNA. This denaturation process is referred to herein as "dehybridization." A MeRPy-tagged amplicon may be dehybridized using any one of the following denaturation buffers: sodium hydroxide, formamide, dimethyl sulfoxide (DMSO) and/or urea. In some embodiments, a dehybridization buffer comprises: sodium hydroxide and ethylenediaminetetraacetic acid (EDTA); formamide and EDTA; or Tris-EDTA (in the presence of heat, e.g., 80-95° C.). Other denaturation buffers are encompassed by the present disclosure.

In some embodiments, a dehybridization solution comprises an alkaline solution, for example a basic dehybridization solution (e.g., BDS, 100 mM NaOH, 1 mM EDTA). In some embodiments, a dehybridization solution comprises a formamide solution, for example, a formamide dehybridization buffer (e.g., FDB, 95% (v/v) formamide, 5 mM EDTA, pH 8.1). In some embodiments, a dehybridization solution comprises dimethyl sulfoxide (DMSO). In some embodiments, a dehybridization solution comprises an aqueous buffer (e.g., Tris-EDTA, TE).

Dehybridization in solution may also include a heating step, for example, heating a dehybridization solution to 80-95° C. (e.g., 95° C.) for 2-5 minutes.

In some embodiments, a MeRPy-tagged amplicon may be dehybridized using physical methods, such as sonication or agitation in the presence of glass beads.

Separation and ssDNA Retrieval

Following dehybridization of MeRPy-tagged amplicon to produce tagged and untagged ssDNA, tagged ssDNA may be separated from the ssDNA-containing solution. This may be achieved using the selective precipitation method described above (e.g., for LC or HMWCC), or by centrifugation or microfiltration (e.g., for HMWCC). Removal of the tagged ssDNA from ssDNA-containing solution is referred to herein as "separation."

Thus, in some embodiments, methods of the present disclosure comprise adding methanol to a solution comprising, for example, dehybridization buffer, tagged and untagged ssDNA, to selectively precipitate the tagged ssDNA. For example, the addition of methanol having of volume of at least 2× (e.g., at least 2×, 2.5×, 3×, 3.5×, 4×, 4.5× or 5×) relative to the total volume of the solution results in selective precipitation of the tagged ssDNA. Thus, in some embodiments, method of the present disclosure comprising adding to a solution comprising tagged and untagged ssDNA at least 2 volumes of methanol. In some embodiments, method of the present disclosure comprising adding to a solution comprising tagged and untagged ssDNA at least 3 volumes of methanol. The precipitate is then collected from solution, leaving a solution of ssDNA, referred to as herein as a "retrieval solution."

Alternatively, tagged DNA can be separated from untagged ssDNA using microfiltration or centrifugation. In some embodiments, a solution comprising tagged and untagged ssDNA is passed over a microfiltration membrane to remove the tagged ssDNA. The microfiltration membrane may be, for example, a cellulosed acetate membrane or a polyethersulfone membrane. In some embodiments, a solution is subjected to centrifugation to remove the copolymer. A solution may be subjected to centrifugation speeds such as ultracentrifugation speeds of, for example, 100000-200000 g for 15-60 minutes.

In some embodiments, a solution is subjected to centrifugation at low speeds (e.g. about 150 g, about 200 g, or about 350 g). In some embodiments, low centrifugation speeds are used in early precipitation steps (e.g. Part I: Strand 1 recovery (native and denaturing precipitations), Examples). In some embodiments, a solution is subjected to centrifugation at high speeds (e.g. about 10,000 g, about 20,000 g or higher). In some embodiments, a high centrifugation speed is important in late precipitation steps (e.g. part II: Strand 2 recovery (UDG/DMEDA strand cleavage), Examples; and part III: Isopropanol precipitation, Examples)

This retrieval solution comprises untagged ssDNA, which may be purified from the solution using standard ethanol or isopropanol precipitation protocols. For example, ssDNA can be purified by precipitation in an alcohol/retrieval solution mixture in the presence of a high concentration (e.g., 0.5-1M LiCl, 0.3-0.5M NaCl, NaOAc, or 2-3 M NH$_4$Ac) of inorganic salt and ethanol or isopropanol (e.g., 30%-50% final percentage isopropanol; 60%-80% final percentage ethanol), storage for a brief period of time at −20° C. or −70° C., followed by centrifugation. Subsequent desalting of the ssDNA pellet may comprise rinsing the pellet in 70% alcohol, recentrifugation and re-suspension in buffer or water.

AB-Site Creation and Cleavage

Figure 2:
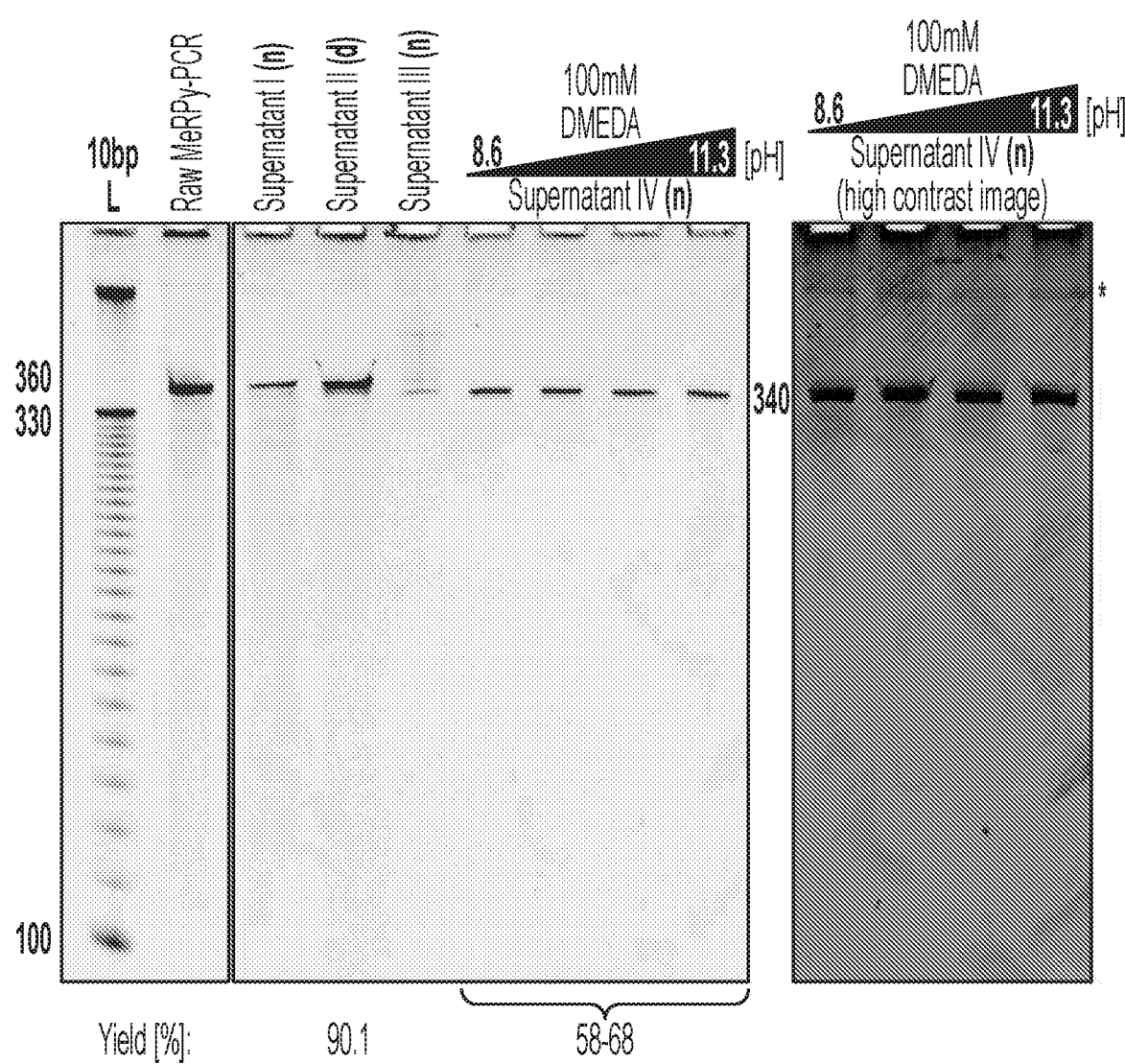
FIG. 2 shows a denaturing polyacrylamide gel electrophoresis (PAGE) analysis of the MeRPy-PCR results. Normal and high contrast images of supernatant IV are shown. (*) These bands are gel artifacts and were seen across all lanes (also empty lanes) of the gel.
Figure 3A:
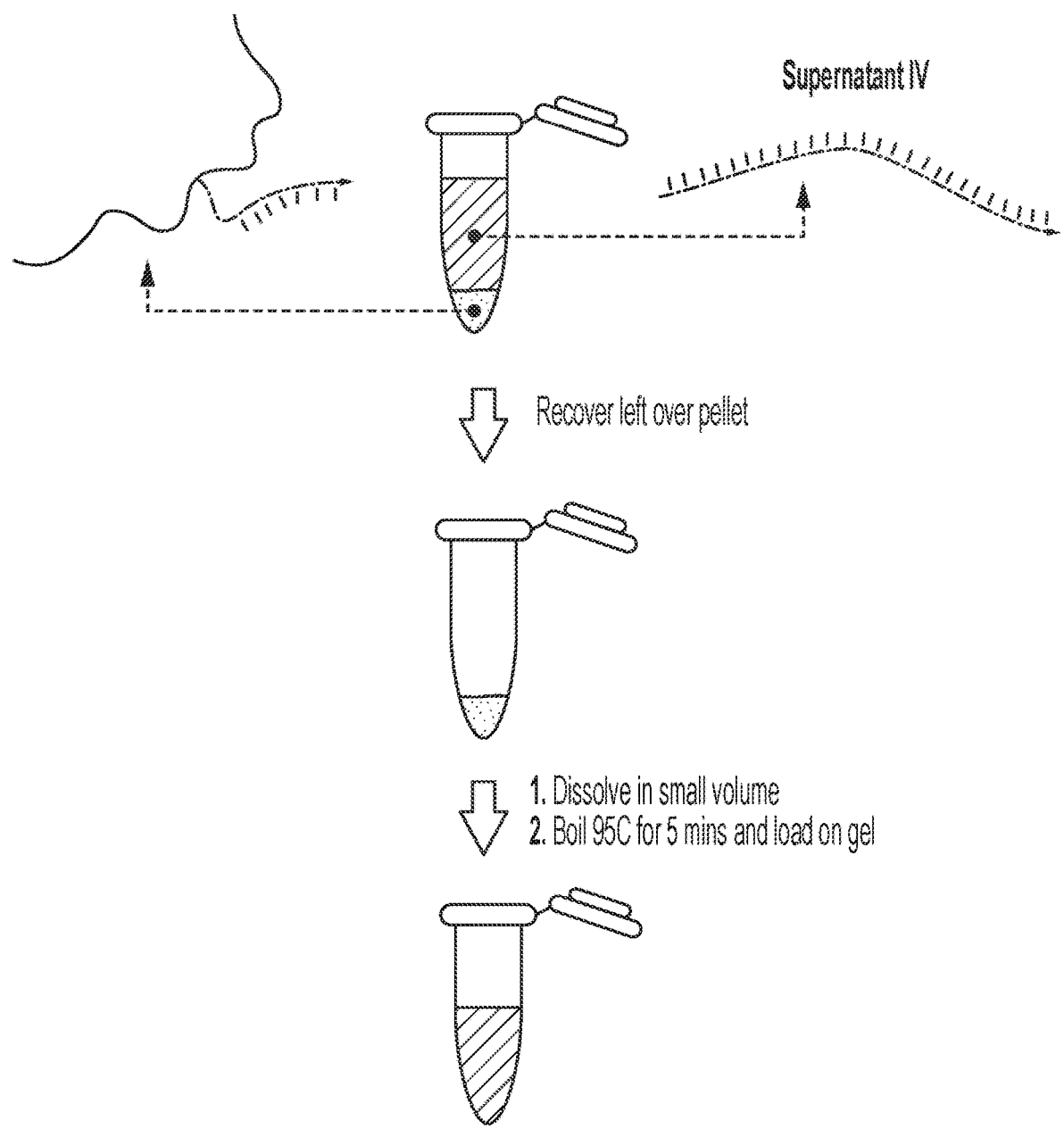
FIG. 3A and FIG. 3B show results from experiments controlling for residual target strand left over in the final MeRPy-PCR pellet.
Figure 3B:
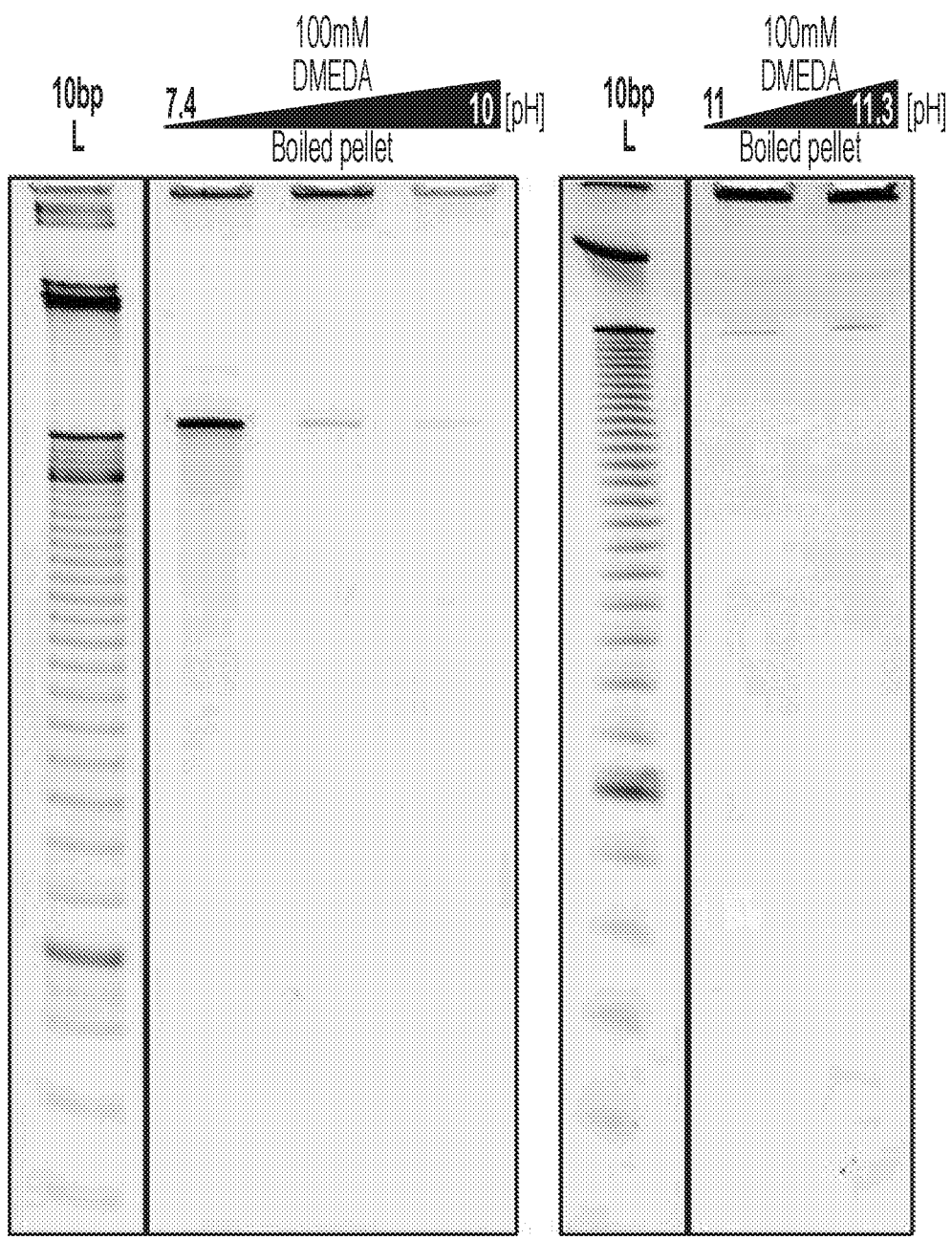

The tagged DNA may be treated with Uracil-DNA Glycosylase (UDG) and UDG reaction buffer to prepare for tag removal. A UDG treatment may include prior selective precipitation under native or denaturing conditions and resuspension in water and 1×UDG reaction buffer, for example. The reaction may be run for 15-30 minutes at 37° C. The tagged DNA may be isolated via selective precipitation under native conditions (e.g., supernatant III) to remove the UDG and UDG reaction buffer. Subsequent addition of DMEDA (e.g., 1 volume of 200 mM; e.g., 1M of 10×DMEDA, buffered to a pH of 7-9) and incubation (e.g., at 37° C. for 15-30 minutes) yields cleavage of the AB-site in the dissolved MeRPy-PCR product (now single stranded) (FIG. 1C). In some embodiments, the cleavage with DMEDA does not require selective precipitation of the tagged DNA prior to addition of the DMEDA. Separation under native conditions (supernatant IV) recovers the target strand (FIG. 2). In general, higher pH of the DMEDA cleavage reagent achieves higher recovery yield (shown in FIG. 3). Heating to 95° C., for example, breaks AB-site and allows for control of residual target strand in the pellet.

It should be understood that while UDG is exemplified herein, other enzymatic cleavage systems may be used. In some embodiments, the MeRPy-tagged primer comprises a cleavage site (e.g., terminal cleavage site or a cleavage site anywhere within the primer sequence). Cleavage sites are specific nucleic acid sequences, nucleotides, or nucleosides at which site-specific enzymes can cleave or cut the sequence such that it is no longer contiguous. In some embodiments, the enzymatic cleavage that can be used for removal of the tag is use of restriction enzymes or use of nicking enzymes. Any suitable specific enzymatic cleavage agent can be used to cleave (or digest off) the tag. Examples of enzymatic cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I, Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind II, Hind III, Hpa I, Hpa II, Kpη I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sea I, ScrF I, Sfi I, Sma I, Spe I, Sph I, Ssp I, Stu I, Sty I, Swa I, Taq I, Xba I, Xho I; glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Nucleic acid may be treated with a chemical agent, and the modified nucleic acid may be cleaved. In non-limiting examples, nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

Preparation of Guide RNA Template

While the present disclosure primarily describes the production of long stretches of ssDNA (e.g., for use in DNA origami methods), shorter stretches may also be produced. Such shorter stretches, for example, less than 100 nucleotides, may be useful for producing ssDNA that is used as template for the production of guide RNAs, which function to target Cas9 endonucleases (and similar endonucleases) to target nucleic acids (e.g., genomic/chromosomal nucleic acids). Thus, in some embodiments, provided herein are methods of producing guide RNA template, the methods comprising (a) combining in solution acrylamide-tagged double-stranded deoxyribonucleic acid (dsDNA) and acrylamide (AA) to form copolymer-linked dsDNA, (b) dehybridizing the copolymer-linked dsDNA to produce in solution free ssDNA and DNA-containing copolymer, and (c)

separating the free ssDNA from the solution of (b), thereby producing ssDNA for use as a template for producing guide RNAs.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

EXAMPLES

The data below demonstrated that MeRPy-PCR can be performed without the need for additional optimization beyond that needed for PCR in general, and can be used to recover high yields of both forward and reverse strands, with a briefer protocol and higher yields for the untagged strand. It was further demonstrated that the generated ssDNA can be used in a variety of demand-meeting applications in synthetic biology, (bio)nanotechnology, and biological imaging. The short time frame to recover the strands is user-friendly and lowers the bar to rapid in-house production of large quantities of ssDNA. Importantly, the low-cost production of strands via MeRPy-PCR may enable the accelerated exploration of scaffold design space in DNA origami, of genome visualization with FISH, and of the efficiency and off-target effects of single stranded donor DNA in CRISPR/Cas9 HDR.

Example 1. ssDNA Production Method

An example ssDNA production method includes the following steps:
1. Sequestration: Acrylamide-tagged ssDNA (containing a deoxyuridine (dU) on the 3'-end of the sequence) is copolymerized with acrylamide monomers, resulting in linear copolymers with high molecular weight (FIG. 1A), we term DNA-tagged methanol responsive polymer (DNA-tagged MeRPy).
2. Purification (optional): Unreacted ssDNA, acrylamide monomers, and other reagents can be removed from the mixture by selective precipitation of the copolymer or by electroelution.
3A. Polymerase chain reaction (PCR) with DNA-tagged MeRPy: The DNA-tagged MeRPy is used as a forward primer in a standard PCR to produce MeRPy-tagged amplicons (FIG. 1B); or
3B. Addition (e.g., ligation, click chemistry, or other linker) of random forward primer sequence to DNA-tagged MeRPy sequence (optional):
   a. Hybridize a ssDNA sequence that acts as a splint strand for the ligation of a random forward primer sequence present with the DNA-tagged MeRPy.
   b. The free (unligated) ssDNA, splint ssDNA, and other reagents can be removed from the mixture by selective precipitation of the copolymer or by electroelution.
   c. The DNA-tagged MeRPy is used as a forward primer in a standard PCR to produce MeRPy-tagged amplicons.
4. Dehybridization: The DNA double strands are dehybridized under denaturing conditions and the complementary untagged strand can be recovered (FIG. 1C).
5. Creation of an abasic site (AB-site): Treatment with uracil-DNA glycosylase (UDG) to create an AB-site from the dU 3'-end of DNA sequence tagged into MeRPy (FIG. 1C).
6. Cleavage of the AB-site: Treatment with N,N'-Dimethylethylenediamine (DMEDA) cleaves the AB-site and liberates the ssDNA (FIG. 1C).
7. Separation and ssDNA retrieval: The copolymer is removed from the released ssDNA by filtration, centrifugation, or selective precipitation (FIG. 1C).

Formation of DNA-Tagged MeRPy

Acrylamide-tagged ssDNA is sequestered from solution by copolymerization with acrylamide monomers. Linear copolymer (LC) is formed by copolymerization of acrylamide (AA) with acrylamide-DNA. The radical polymerization is initiated by ammonium persulfate (APS) and catalyzed by tetramethylethylenediamine (TEMED). The sequestration is complete after overnight polymerization but can also be completed in less than 2 hours. The LC can be separated from the solution by selective precipitation.

Standard PCR

A 360-bp template DNA was combined with the DNA-tagged MeRPy (containing DNA complementary to the template DNA) as a forward primer, a reverse primer, dNTPs, and buffer to produce a "raw" MeRPy PCR product (amplicon).

Separation and ssDNA Retrieval

The raw MeRPy-PCR product was mixed with untagged MeRPy (linear acrylamide polymer without acrylamide-tagged ssDNA) and separated under native conditions (supernatant I), removing untagged contaminants (FIG. 1C). Separation under denaturing conditions released the complementary untagged ssDNA (supernatant II) (FIG. 1C).

Selective Cleaving of an AB-Site

The tagged DNA was treated with Uracil-DNA Glycosylase (UDG) and UDG reaction buffer. UDG treatment involved prior selective precipitation under native or denaturing conditions and resuspension in water and 1×UDG reaction buffer. The reaction was run for 15-30 minutes at 37° C. The tagged DNA was separated via selective precipitation under native conditions (supernatant III) to remove the UDG and UDG reaction buffer. Subsequent addition of 1 volume of 200 mM DMEDA and incubation at 37° C. for 15-30 minutes yielded in the cleavage of the AB-site in dissolved MeRPy-PCR product (now single stranded) (FIG. 1C). Separation under native conditions (supernatant IV) recovered the target strand (FIG. 2). FIG. 2 shows the MeRPy-PCR results. Recovery of the complementary (untagged strand—109-3315 nt (e.g., 360 nt)) is possible with over 90% yield. Cleavage of the AB-site and recovery of the tagged strand (89-3095 nt (e.g., 340 nt)) is possible with up to 80% yield. In general, higher pH of the DMEDA cleavage reagent achieves higher recovery yield (shown in FIG. 3). The final pellet (after decanting supernatant IV) was dissolved in 100 μL water and heated to 95° C. for 5 minutes. Heating to 95° C. breaks AB-site and allows for control of left-over target strand in the pellet.

5'-End Purification of Synthetic Oligonucleotides

Figure 4A:
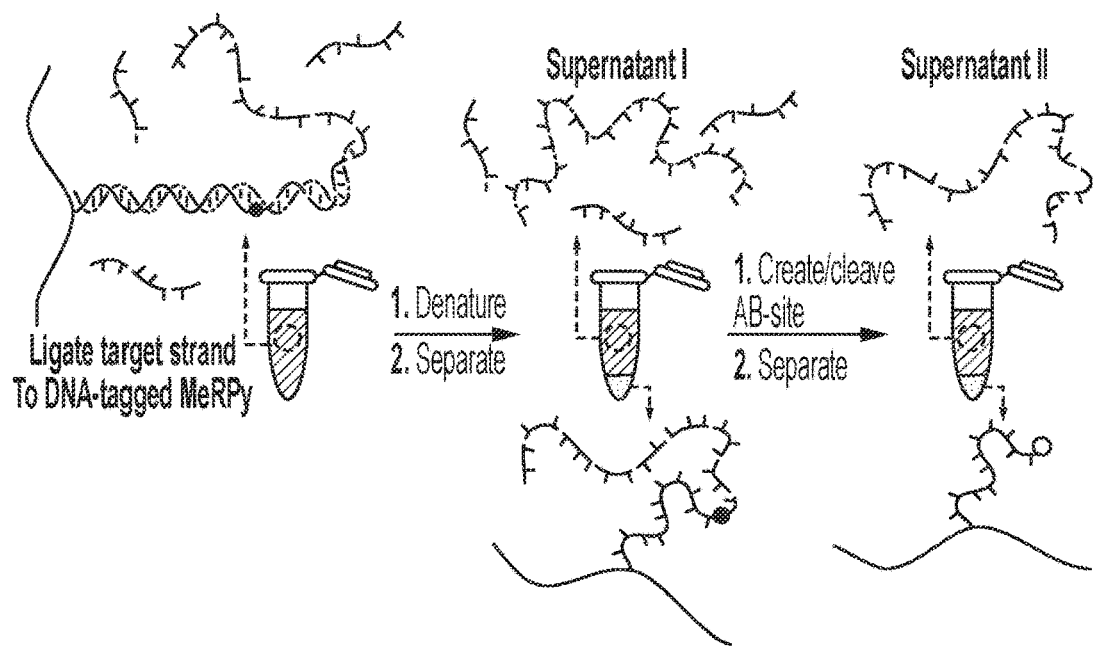
FIG. 4A and FIG. 4B show the purification of synthetic ssDNA via the DNA-tagged MeRPy.
Figure 4B:
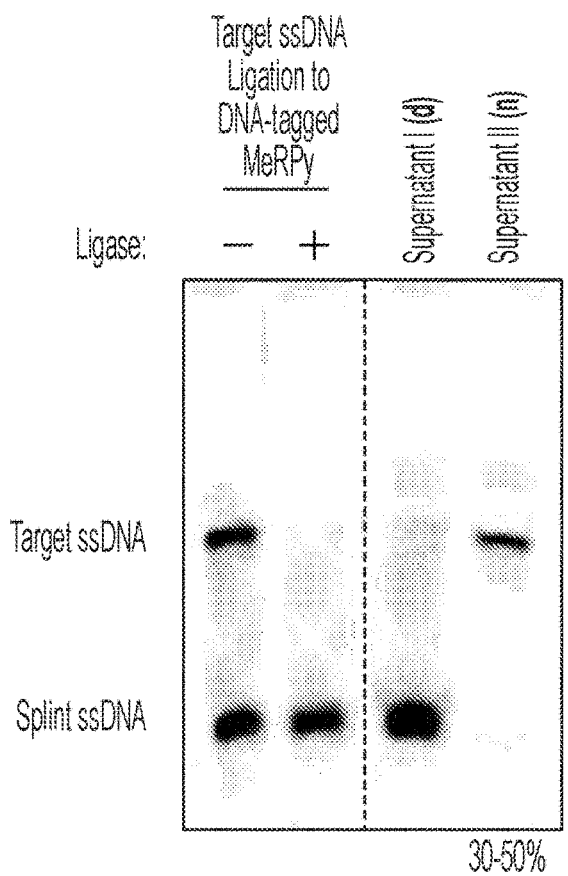

Selective 5'-end purification of synthetic oligonucleotides is shown in FIG. 4A and FIG. 4B. It is possible to ligate the target strand onto the DNA-tagged MeRPy and selectively purify for 5'-end truncations. Yields of up to 50% were achieved using this method (FIG. 4B).

3'-End Purification of Synthetic Oligonucleotides

Selective 3'-end purification of synthetic oligonucleotides may also be achieved by using DNA-tagged MeRPy.

Example 2. Methanol-Responsive Polymer PCR (MeRPy-PCR)

Figure 5A:
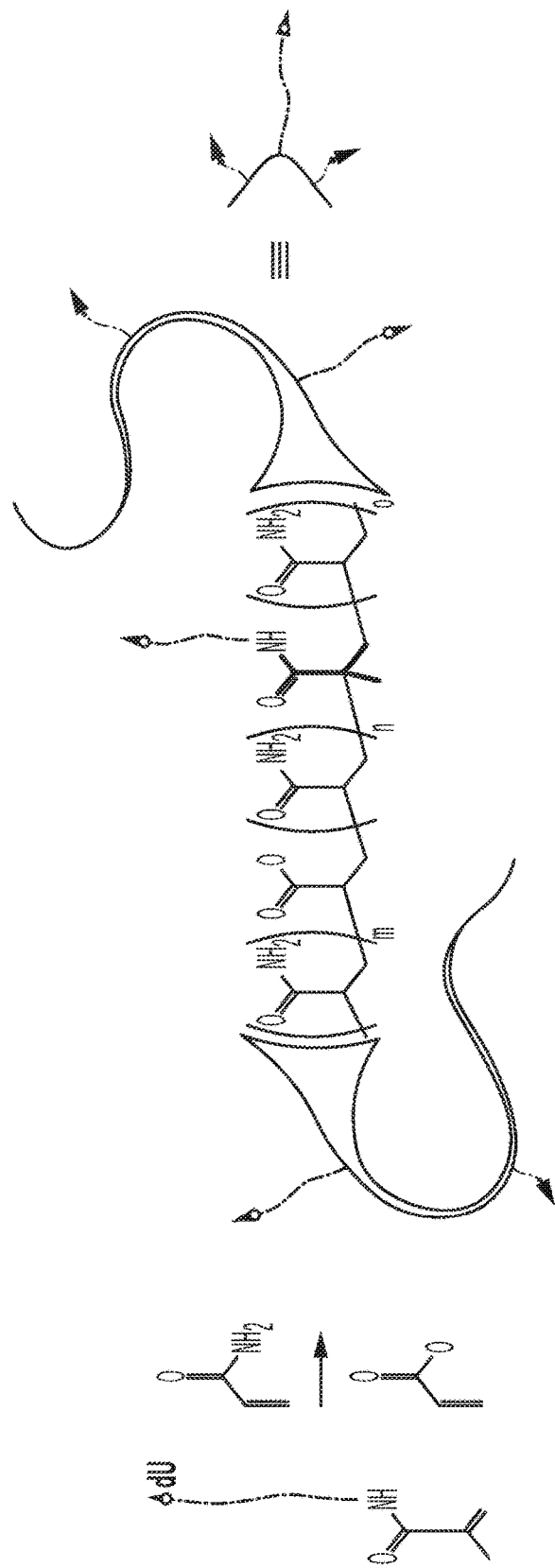
FIGS. 5A-E show a MeRPy-PCR overview and recovery yields for strands 1 (untagged) and 2 (initially tagged) of different amplicon lengths.
Figure 5B:
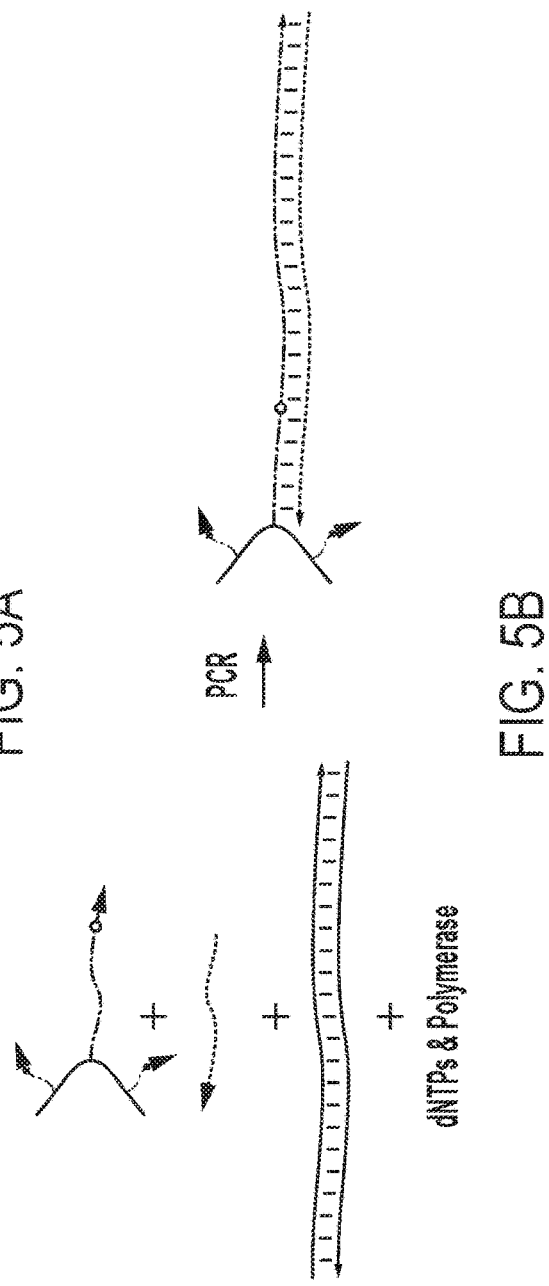
Figure 5C:
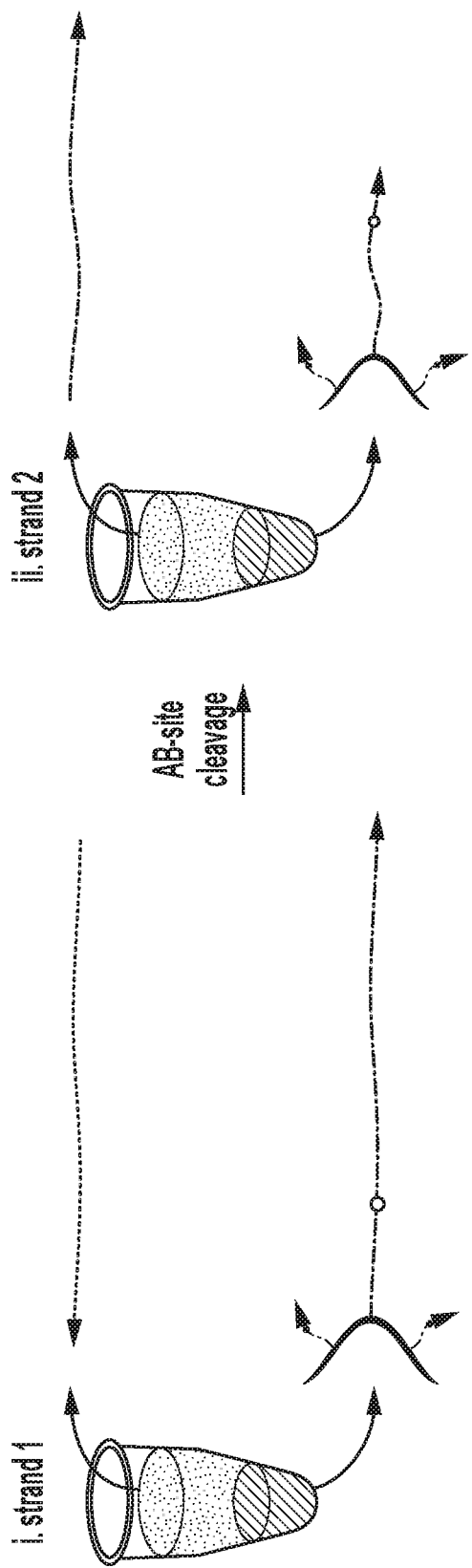
Figure 7:
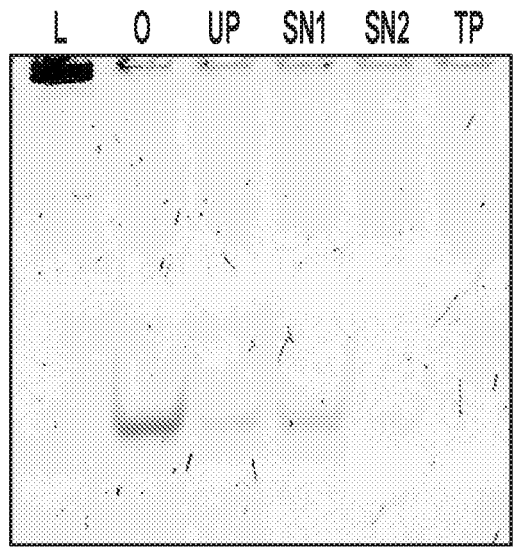
FIG. 7 shows native polyacrylamide gel electrophoresis of tagged primer and supernatants. (L) 1 kb DNA ladder, (O) acrydite tagged primer oligo, (UP) unpurified polymer tagged primer, (SN1) supernatant 1 after first native precipitation clean up, (SN2) supernatant 2 after second native precipitation clean up, (TP) purified polymer tagged primer. Capture yield was quantified by the amount of primer that was not incorporated into the polymer and thus migrated into the native PAGE.
Figure 8:
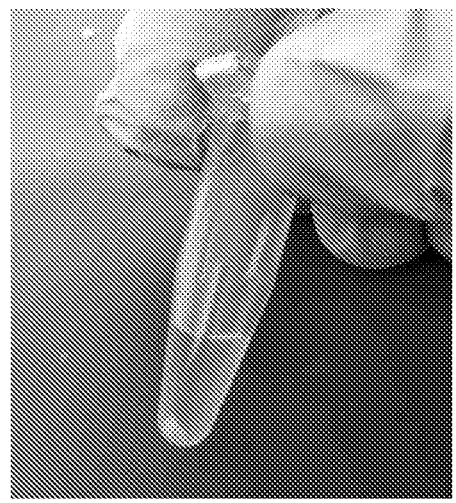
FIG. 8 shows the typical size of a precipitated polymer-pellet with the dsDNA amplicon under native conditions (for 100 μL MeRPy-PCR).
Figure 9:
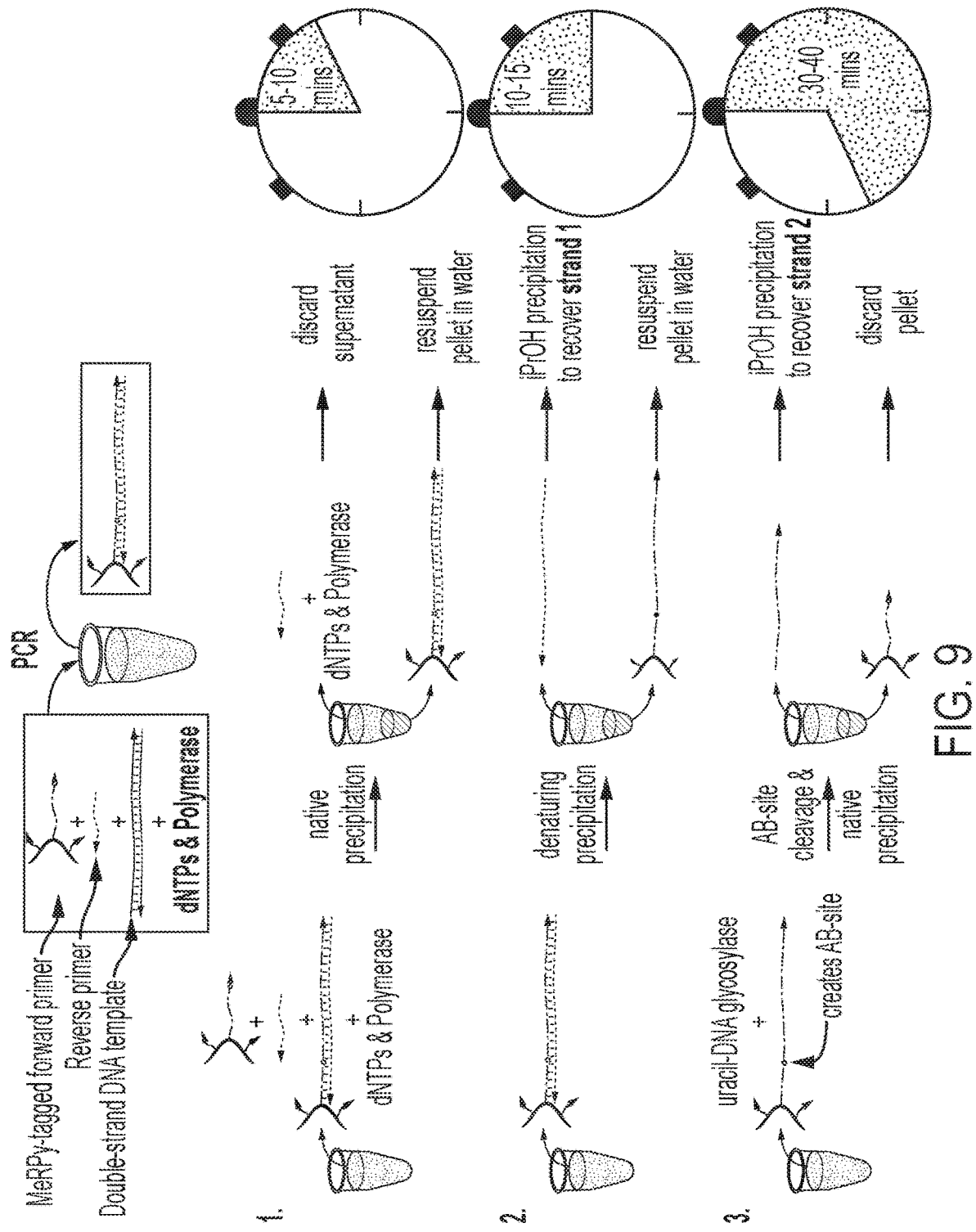
FIG. 9 shows the general procedure for the recovery of ssDNA. A standard PCR reaction generates the tagged amplicon with the MeRPy-tagged DNA acting as a primer in the reaction. (1) Addition of linear polymer without DNA handles (e.g. to a final concentration of approximately 0.25 wt %), water and methanol crashes out the tagged amplicon, followed by discarding the supernatant including reverse primer, dNTPs, and polymerase. (2) Addition of NaOH and water denatures the amplicon and allows the recovery of strand 1 after the addition of methanol. (3) Incubation of the tagged strand 2 with UDG, subsequent cleavage with DMEDA and precipitation with methanol allows the recovery of strand 2.
Figure 10:
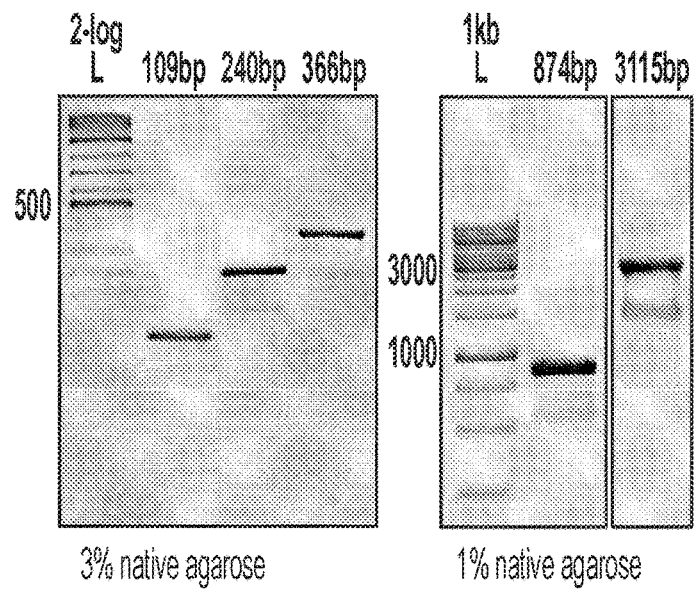
FIG. 10 shows native agarose gel electrophoresis for standard PCR amplicons (dsDNA) on templates used for MeRPy-PCR ssDNA production (shown in FIG. 5).
Figure 11:
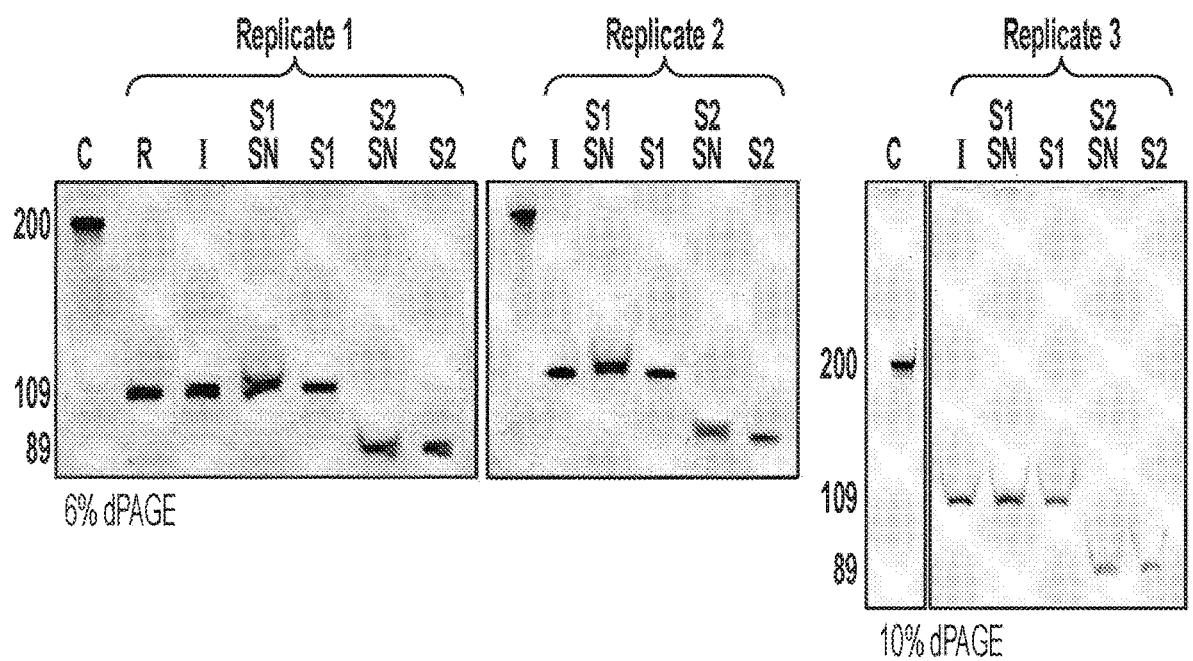
FIG. 11 shows low range ssDNA recovery with 109 bp template. (C) 200 nt Control oligo from IDT, (R) raw MeRPy-PCR reaction, (I) MeRPy-PCR reaction after first native precipitation, (S1 SN) supernatant after denaturing precipitation of strand 1, (51) strand 1 after iPrOH precipitation, (S2 SN) supernatant after UDG/DMEDA cleavage of strand 2, (S2) strand 2 after iPrOH precipitation.
Figure 12:
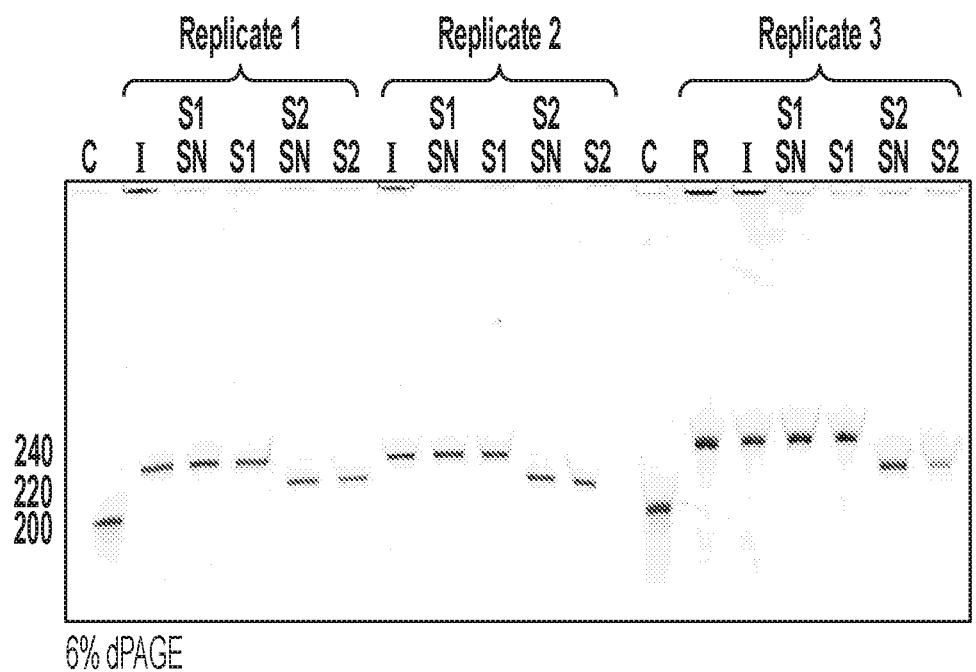
FIG. 12 shows low range ssDNA recovery with 240 bp template. (C) 200 nt Control oligo from IDT, (R) raw MeRPy-PCR reaction, (I) MeRPy-PCR reaction after first native precipitation, (S1 SN) supernatant after denaturing precipitation of strand 1, (51) strand 1 after iPrOH precipitation, (S2 SN) supernatant after UDG/DMEDA cleavage of strand 2, (S2) strand 2 after iPrOH precipitation.
Figure 13:
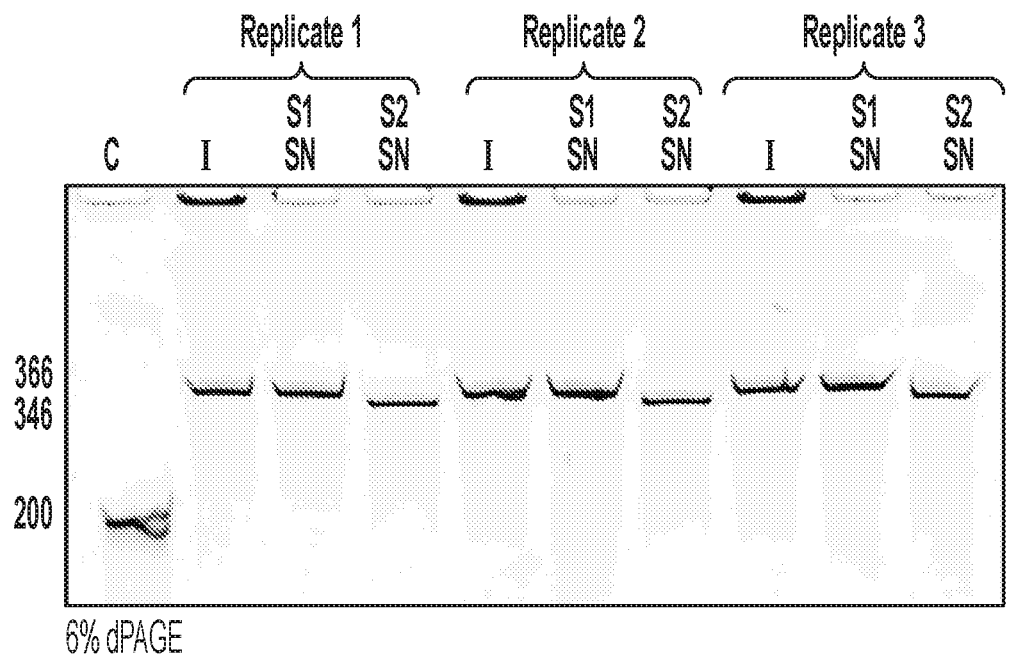
FIG. 13 shows low range ssDNA recovery with 366 bp template. (C) 200 nt Control oligo from IDT, (I) MeRPy-PCR reaction after first native precipitation, (S1 SN) supernatant after denaturing precipitation of strand 1, (S1) strand 1 after iPrOH precipitation, (S2 SN) supernatant after UDG/DMEDA cleavage of strand 2, (S2) strand 2 after iPrOH precipitation.
Figure 14:
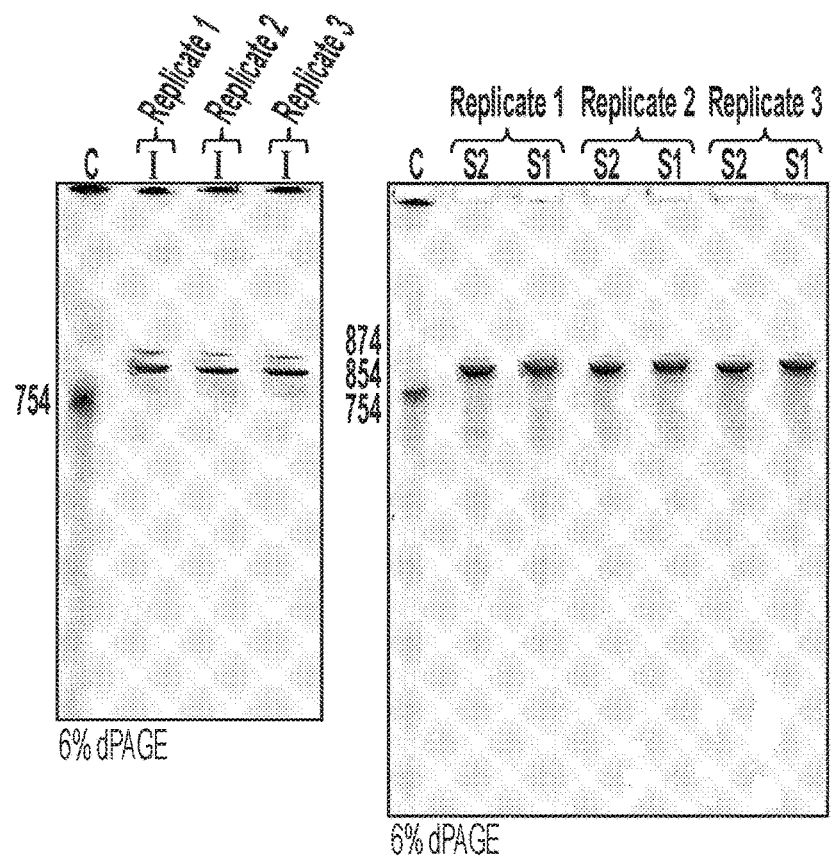
FIG. 14 shows mid-range ssDNA recovery with 874 bp template. (C) 754 nt Control oligo from IDT, (I) MeRPy-PCR reaction after first native precipitation, (S1) strand 1 after iPrOH precipitation, (S2) strand 2 after iPrOH precipitation.
Figure 15:
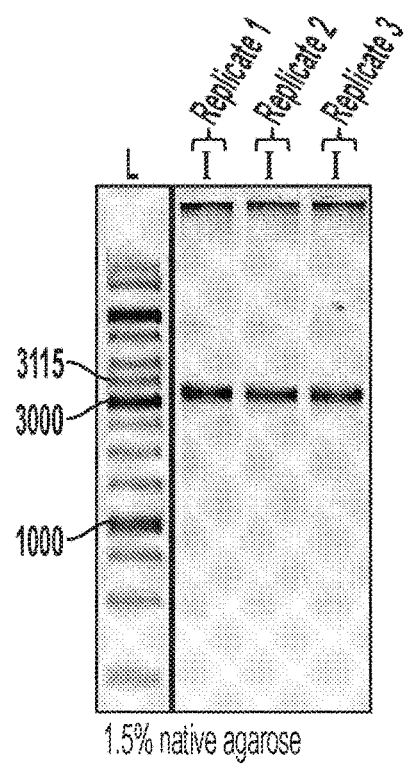
FIG. 15 shows high range ssDNA recovery with 3,115 bp template. (L) 1 kb ladder, (I) MeRPy-PCR reaction after first native precipitation.

The present disclosure presents a method that is referred to as Methanol-Responsive Polymer PCR (MeRPy-PCR). Herein, a set of primers bearing a linear polyacrylamide-co-acrylate tag were created by co-polymerizing a 5'-acrydite-modified primer with acrylamide and sodium acrylate (FIG. 5A, FIG. 7, Table 1). It was demonstrated that the modified primer can include a deoxyuridine (dU), which can be placed anywhere along the sequence and allows the site-specific creation and subsequent cleavage of an abasic site (AB site). The polymer-tagged primer was used in an otherwise standard PCR reaction, resulting in a polymer-tagged amplicon (FIG. 5B, Example 3) that subsequently allows the selective precipitation (FIG. 8) and recovery of both sense and antisense strands away from each other (FIG. 5C, FIG. 9). It was also found that the substitution of a polymer-tagged primer had no noticeably adverse effects on PCR production in terms of strand yield and purity (FIG. 10).

After the MeRPy-PCR step, polymer without DNA handles (e.g., linear acrylamide polymer without acrylamide-tagged ssDNA) may be added up to a final concentration of approximately 0.25 wt % to aid in precipitation in the following recovery step.

After PCR, untagged strand 1 was recovered in a supernatant by performing a denaturing precipitation under alkaline conditions by addition of NaOH to 44 mM final concentration, followed by mixing with one volume equivalent of methanol and then centrifugation at 350-2,000 RCF (FIG. 5Ci). Next, complementary strand 2 was recovered by resuspending the precipitated polymer-DNA pellet and incubating it with uracil-DNA glycosylase (UDG) for 15 minutes to excise the dU nucleobase and create an AB site. The AB site was then cleaved by incubating the polymer-DNA solution with 100 mM dimethylethylenediamine (DMEDA)[11] for 15 minutes, followed by precipitation in 50% methanol to remove the waste polymer-tagged DNA (FIG. 5Cii). The procedure was completed within ~45-65 minutes (depending on strand amplicon length), with strand 1 recovery accounting for the first ~15-25 minutes (FIG. 9).

Figure 5E:
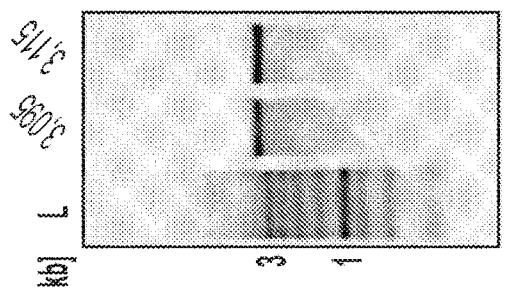
Figure 5E:
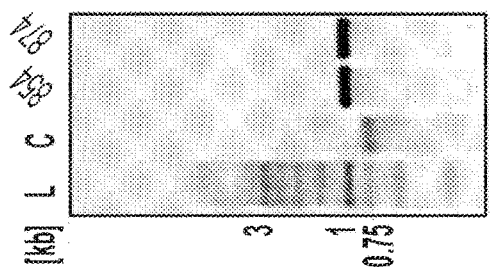
Figure 5E:
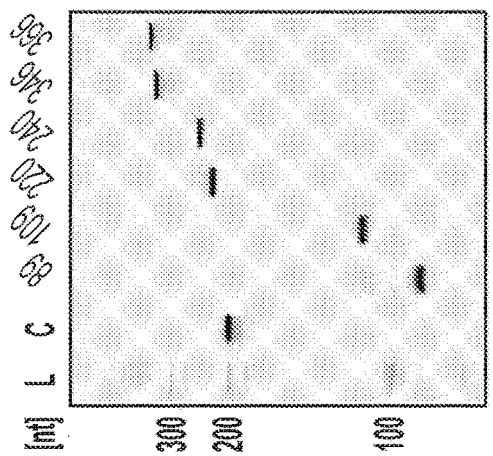
Figure 5D:
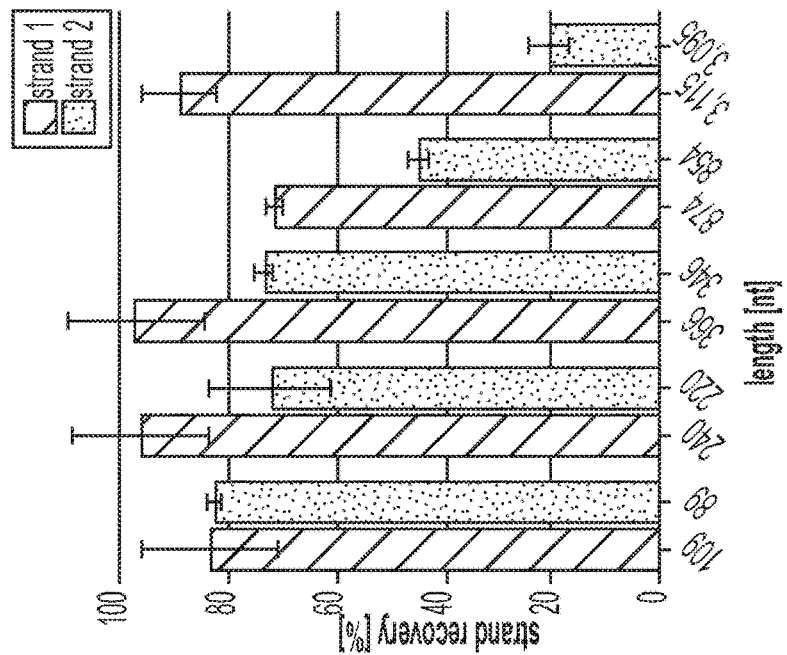
Figure 16:
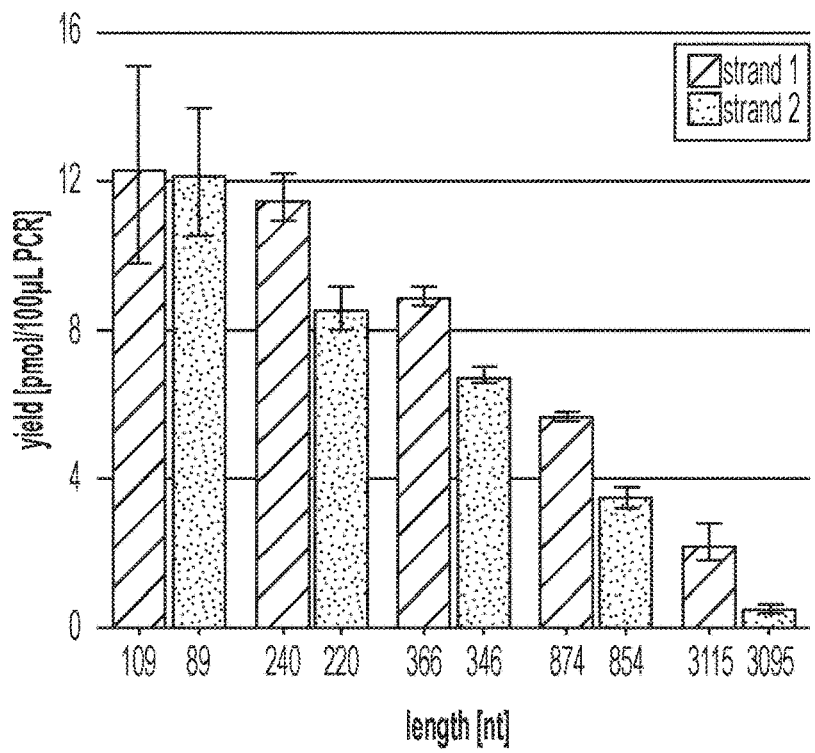
FIG. 16 shows absolute recovery yield for strand 1 and 2 of various lengths. Bar graphs denoting the recovery yield (pmol/100 μL MeRPy-PCR reaction). Strand recovery yield was determined by nanodrop after the iPrOH precipitation. Data is shown as mean+/−STD (N=3).

The method presented herein was used to generate ssDNA ranging from 89-3115 nt in length by amplifying an array of target sequences with MeRPy-PCR and recovering both strands 1 and 2 of each amplicon (FIG. 5D, FIGS. 11-15, Example 4-"Recovery Yield of Strand 1 and 2"). The strand-recovery protocol was nearly identical for all lengths and templates, apart from slight differences in the alkaline denaturation step for the longest amplicons (see Example 4). Strand 1 was routinely recovered with a yield of 70% to >90% with respect to the initial MeRPy-PCR amplicon. By contrast, recovery yield of strand 2 was lower as the length of the amplicons increased (see Example 4—"Effect of NaOH denaturation on the recovery yield of strand 2"). Absolute yields of ~2.2-12 pmol/100 μL PCR were recorded for strand 1 and ~0.5-12 pmol/100 μL PCR for strand 2 (FIG. 16). It was noted that the final amount and purity of recovered ssDNA depends on the efficiency and cleanliness of the PCR, therefore PCR optimization may be desirable in the methods presented herein. Furthermore, it was observed that ssDNAs recovered from MeRPy-PCR were of high purity, on par or better than a chemically-synthesized 200mer oligonucleotide after PAGE purification and an enzymatically produced 754mer oligonucleotide purchased from the commercial vendor Integrated DNA Technologies (FIG. 5E).

Example 3. CRISPR/Cas9 Mediated Homology Directed Repair (HDR)

To demonstrate the utility of MeRPy-PCR generated ssDNA for demand-meeting applications, the present disclosure shows CRISPR/Cas9 mediated homology directed repair (HDR) in human cells, fluorescent in situ hybridization (FISH) imaging, and DNA-origami folding. The untagged strand 1 for each application was picked based on the higher overall recovery yield and briefer protocol. It is known in the art that each of the three tested applications utilizes ssDNA in varying capacities; DNA origami requires long ssDNA scaffolds (>1 kb)[12-14], FISH requires a library of >100 nt Cy3-labeled strands to tile specific regions of the genome[15], and CRISPR/Cas9 directed HDR has seen growing interest in the field to use long ssDNA over dsDNA donors[16-18], which can be difficult to produce or else prohibitively expensive to purchase at sufficient scale for cell-culture experiments.

Figure 6A:
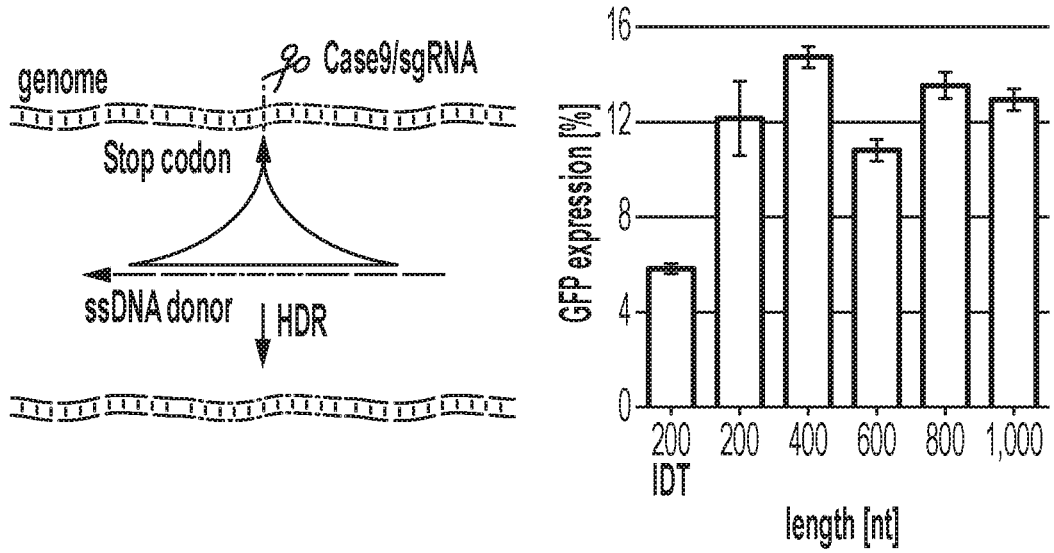
FIGS. 6A-C show applications using ssDNA of various lengths.
Figure 17:
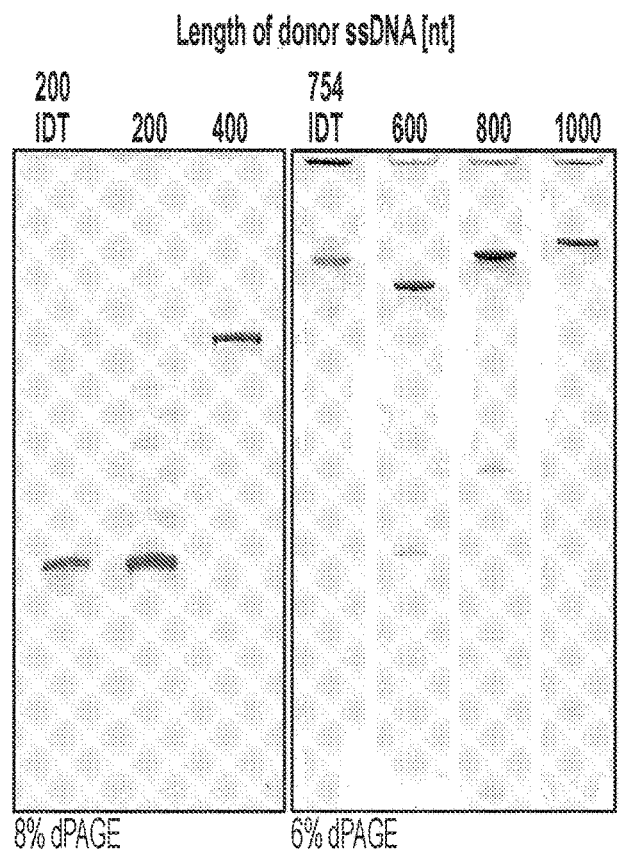
FIG. 17 shows denaturing polyacrylamide gel electrophoresis of ssDNA donor oligos (made with MeRPy-PCR) used in genome editing in human cells using CRISPR/Cas9. Control lanes on both gels are indicated by 200 and 754 nt from IDT.
Figure 18:
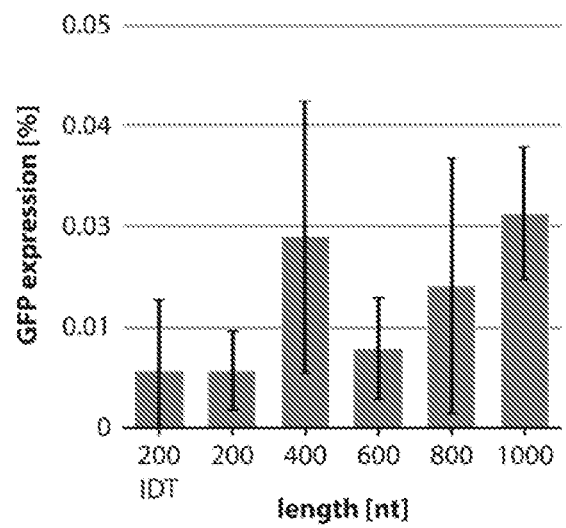
FIG. 18 shows control experiments for genome editing in human cells using CRISPR/Cas9. Bar graphs showing GFP expression for cell populations transfected with ssDNA oligo donor alone. Data is shown as mean+/−STD (N=3).

For HDR, the performance of MeRPy-PCR generated ssDNA donors (FIG. 17) of varying size was assessed relative to a purchased chemically synthesized 200 nt donor from IDT. The ssDNA donor-mediated HDR removed a stop codon from a broken GFP expression vector, restoring the GFP sequence and expression (FIG. 6A, FIG. 18, Example 6—"Fluorescence-activated cell sorting (FACS) scatter plots"). Five different ssDNA donors 200-1000 nt long were generated, only varying the homology-arm length. The ssDNA donors were produced at yields of ~13-34 pmol/100 μL PCR (Table 3). The efficiency of HDR was comparable for the different MeRPy-PCR generated ssDNA and the 200 nt chemically synthesized donor.

Example 4. DNA-Origami Folding

Figure 6B:
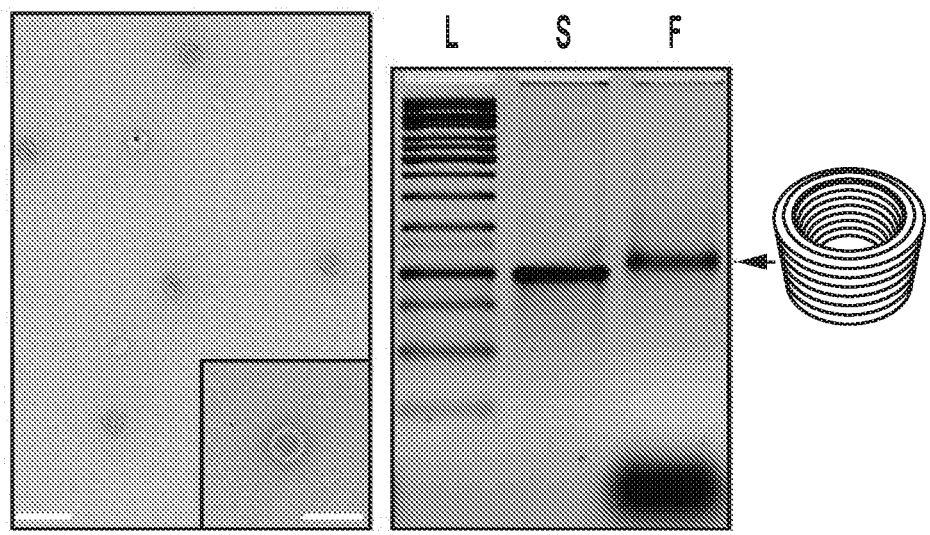
Figure 19:
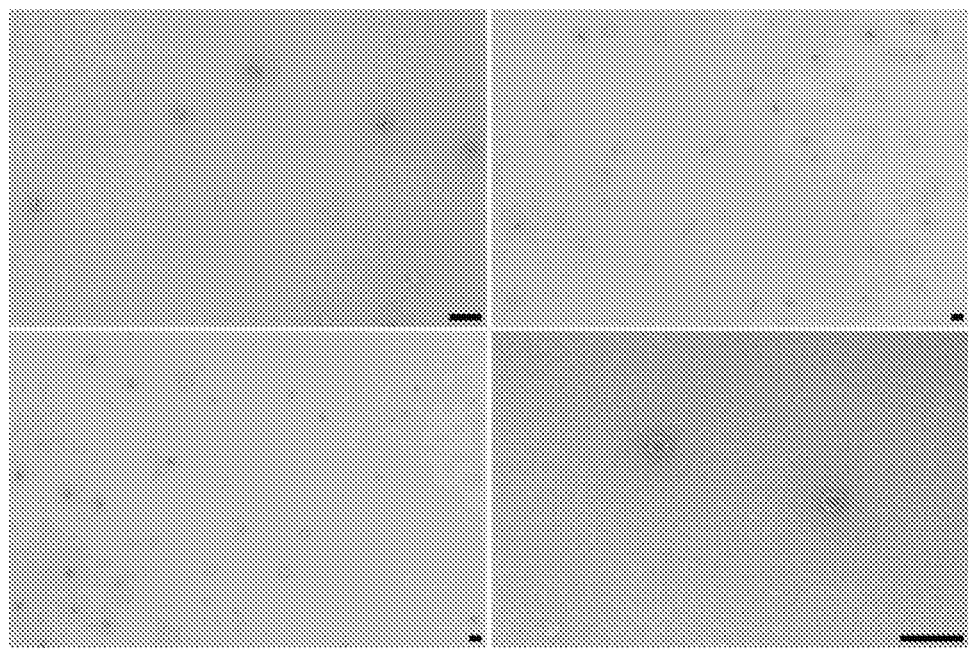
FIG. 19 shows TEM (transmission electron microscopy) micrographs of DNA origami 30 nm barrel structures. Scale bars denote 100 nm.
Figure 20:
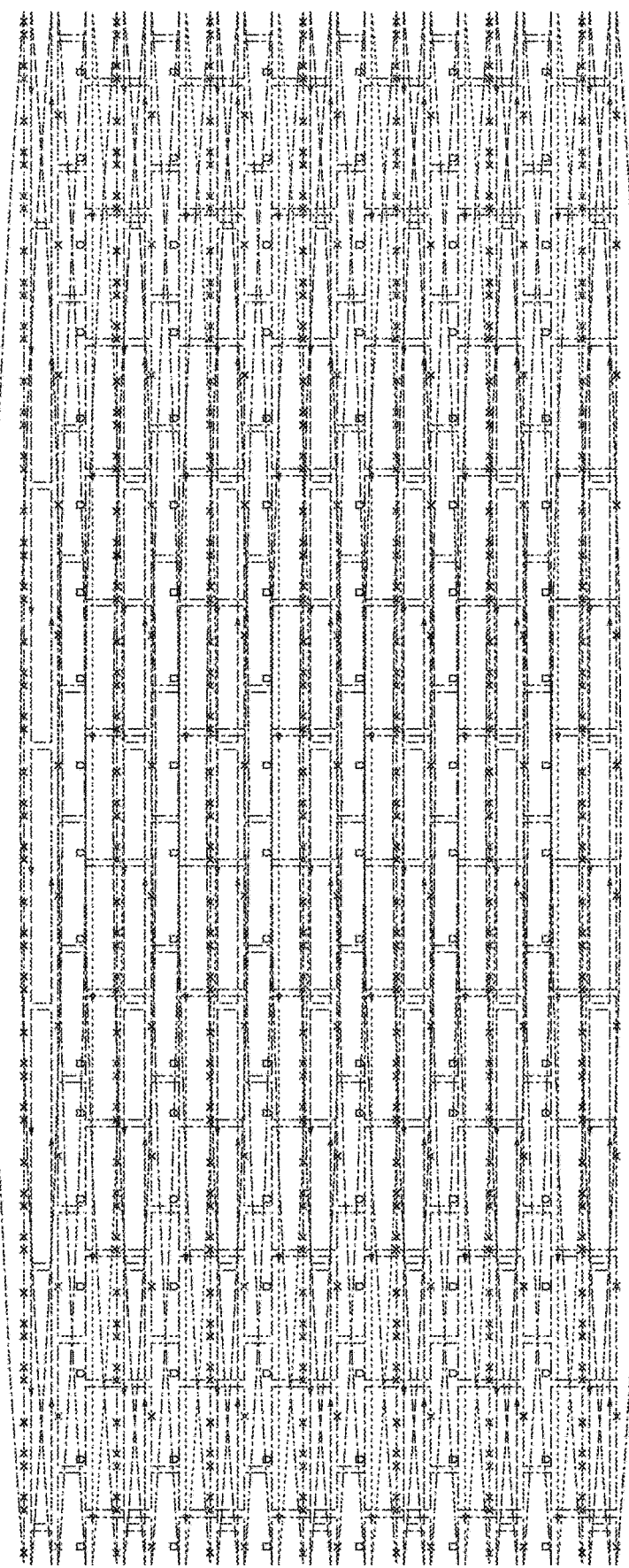
FIG. 20 shows a DNA origami strand diagram (generated with caDNAno; see, for reference, Douglas, S. M., et al. Nucleic Acids Res. 37, 5001-5006 (2009)) of 30 nm barrel (see, for reference, Ponnuswamy, et al. Nat. Comm. 8, 15654 (2017)).

Next, the ability to produce custom scaffolds for DNA-origami folding was tested. DNA origami is often limited to a defined number of ssDNA scaffolds based on the availability of different M13 phage genomes. There is growing interest in the field for the design and production of new scaffolds that offer a larger range of sequence space[19]. To address this application, MeRPy-PCR was first used to generate a 3315 nt ssDNA derived from p7308 M13 genome (Table 4). Using the produced ssDNA scaffold (1.35 pmol/100 μL PCR, Table 5) folding of a DNA-origami barrel[20] was demonstrated (FIG. 6B, FIGS. 19 and 20).

Example 5. FISH Probe Library Generation

Figure 6C:
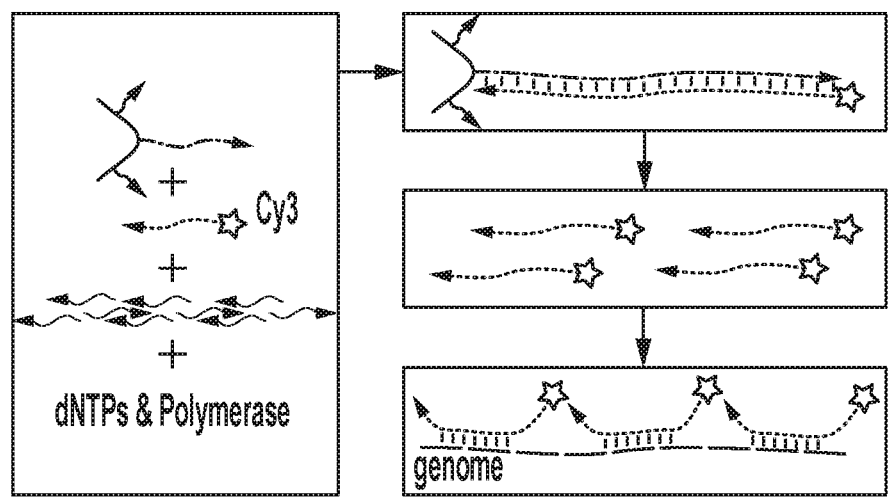
Figure 6C:
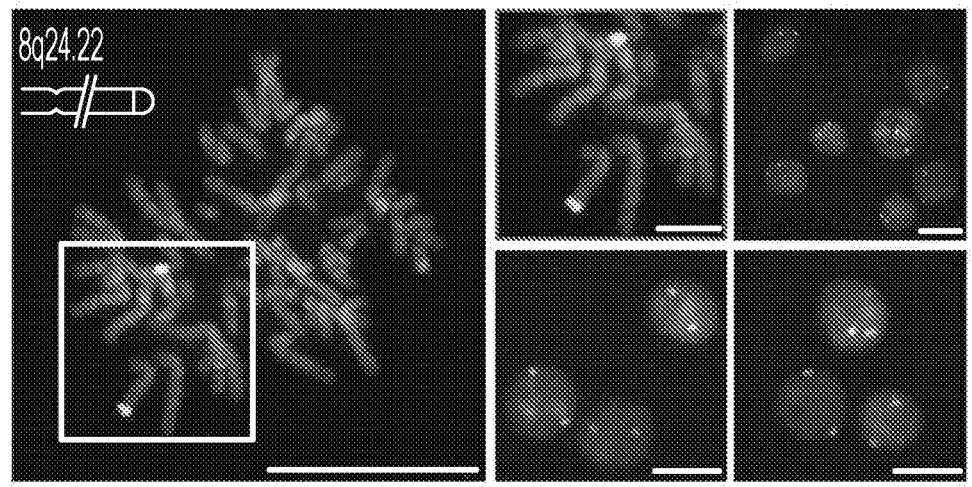
Figure 21:
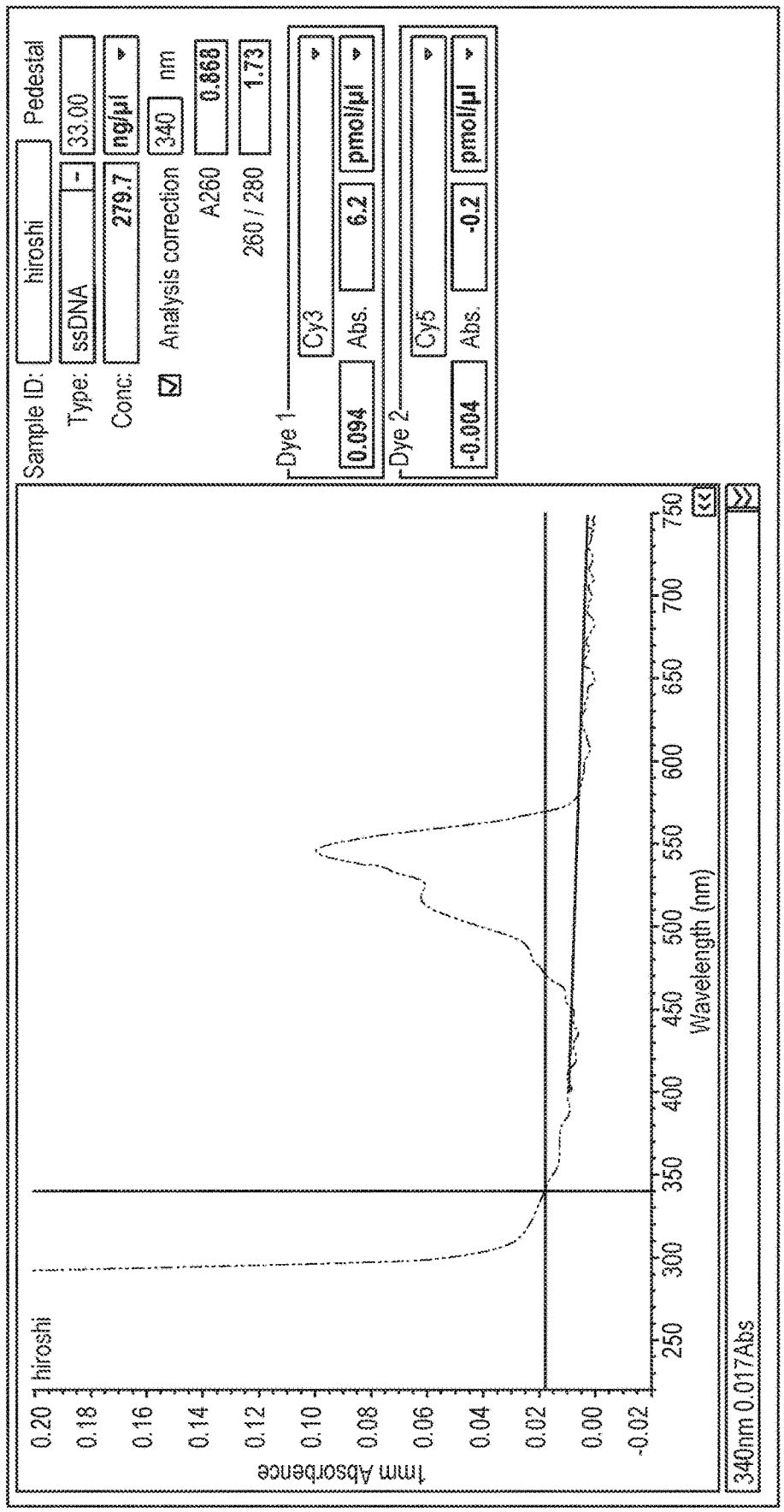
FIG. 21 shows the absorbance spectrum of Cy3-labeled MeRPy-PCR derived ssDNA FISH library.
Figure 22:
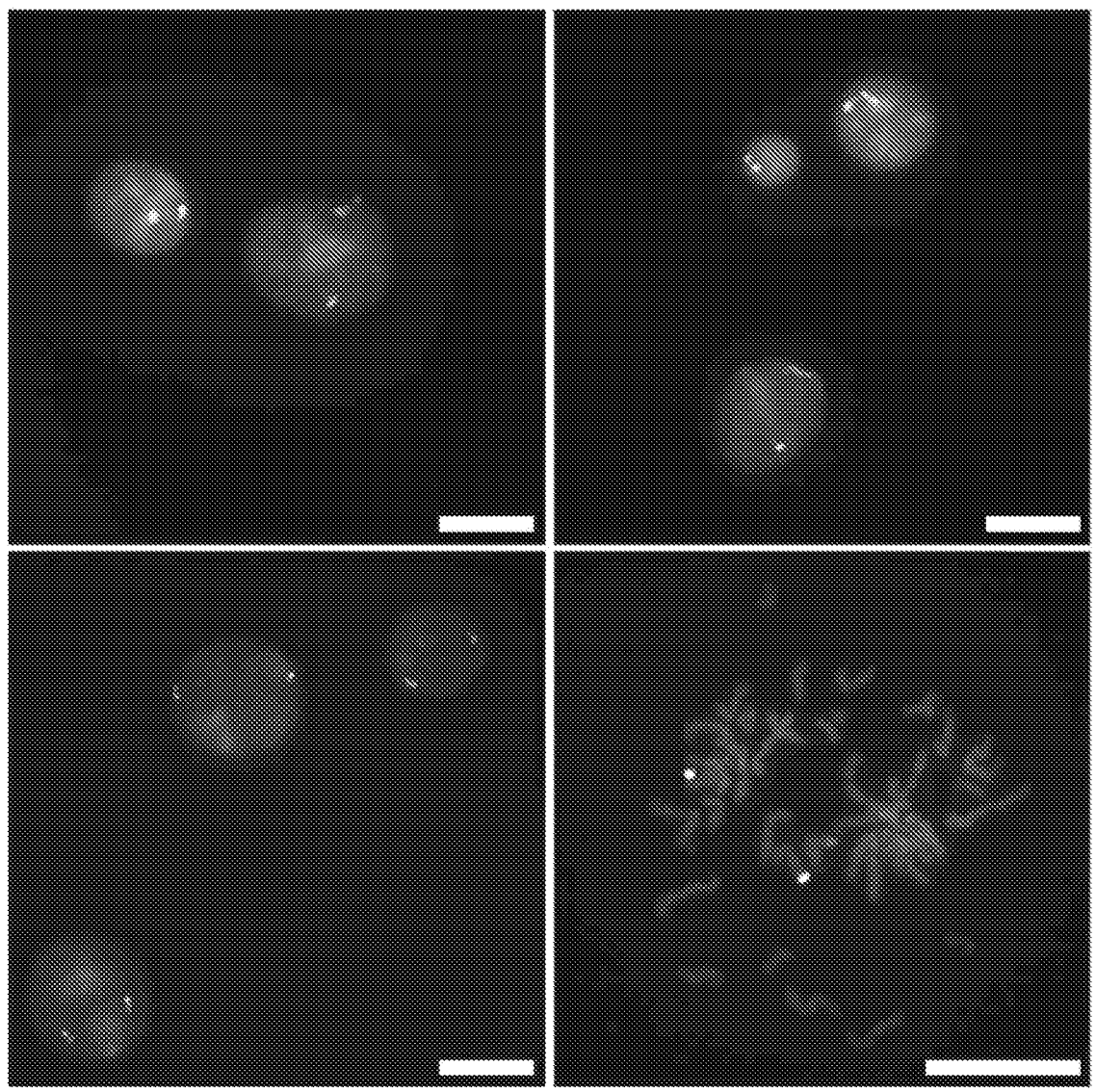
FIG. 22 shows a library comprising 42,000 probe sequences designed to tile along an 8.4 Mbp region of Human Chromosome 8 was amplified from a small amount of template using MeRPy-PCR with a Cy3-labeled reverse primer and subsequent recovery of fluor-tagged strand 1 library. The generated fluor-labeled ssDNA library was validated in situ on fixed human metaphase spreads and interphase cells. Scale bars denote 20 μm.

Finally, the ability to use MeRPy-PCR to generate a large library of FISH probes with a Cy3 modified 5' end was demonstrated (FIG. 6C, FIG. 21). The ability to generate ~70 pmol/100 μL PCR of Cy3-modified ~130 nt FISH probes (Table 6), that can successfully be used in imaging a distinct locus of the genome (Chromosome 8q24.22)[14] was demonstrated. As expected by the FISH probe design, two puncta were observed per cell, with the puncta located towards the end of two similarly sized, medium-length chromosomes (FIG. 6C, FIG. 22). Use of MeRPy-PCR here highlights the ease with which FISH probes can be generated in sufficient quantities for imaging, obviating the need for expensive and time-consuming purifications.

Materials and Methods for Examples 2-5

Solvents and reagents for MeRPy-PCR: All solvents and reagents were purchased from commercial vendors. Methanol (Sigma Aldrich, 322415), Isopropanol (Fisher Scientific, A426P-4), 1,2-Dimethylethylenediamine (Sigma Aldrich, D157805-5G), Molecular biology grade glycogen (Thermo Fisher, R0561), Molecular biology grade acrylamide 40 wt % (Sigma Aldrich, 1697-500 ML), Sodium acrylate (Sigma Aldrich, 408220-35G), Molecular biology grade tetramethylethylenediamine (Life Technologies Corp, 15524010), Ammonium persulfate (Sigma, A3678-25G). All acrylamide-labeled single-stranded and ultramer/megamer DNA was purchased from Integrated DNA Technologies. All double-stranded DNA templates used were purchased from Twist Bioscience. Taq DNA polymerase (NEB, M0273L), Phusion (NEB, M0531S).

UV/Vis absorbance: Nanodrop 2000c Spectrophotometer (Thermo Scientific) was used to record the data.

Agarose gel electrophoresis (AGE): UltraPure agarose (Life technologies, 16500500) was used to prepare agarose gels of various percentages. DNA-Origami structures were eluted for 3 hours at 60 V in pre-stained ethidium bromide (Bio Rad, 1610433) gels in 0.5×TBE buffer containing 11 mM $MgCl_2$. Double-stranded and single-stranded DNA was eluted in 0.5×TBE buffer at 150 V for 1-1.5 hours (depending on the size of the oligo and percentage of gel). Gels were either pre-stained with ethidium bromide (Bio Rad, 1610433) or post-stained with SYBR Gold (Thermo Fisher, S-11494).

Denaturing and native polyacrylamide gel electrophoresis (dPAGE and nPAGE): UreaGel System (National Diagnostics, EC-833-2.2LTR) was used to prepare denaturing polyacrylamide gels of various percentages. 40 wt % acrylamide (Fisher Scientific, BP1406-1) was used to prepare native polyacrylamide gels of 20%. Gels were eluted at 200-300 V for 20-40 minutes (depending on the size of the oligo and percentage of gel) and post-stained with SYBR Gold (Thermo Fisher, S-11494) for 20 minutes before imaging. Densitometry analysis of DNA bands was performed with ImageJ (v2.0.0-rc-69/1.52i) (see, for reference, Schindelin, J. et al. Nat. Meth. 9, 676-682 (2012)).

Transmission electron microscopy (TEM): 3 μL of the crude DNA origami folding reaction was applied to a FCF400-CU-50 TEM grid (Fisher Scientific, 5026034) and incubated for 2 minutes, followed by 3 μL of 2% uranyl formate solution containing 25 mM NaOH and air drying. Imaging was performed at 80 kV on a JEOL JEM 1400 plus.

Polymerase chain reaction (PCR) and DNA origami folding: A PTC-225 Peltier Thermal Cycler (MJ Research) in conjunction with various thermocycler protocols.

Metaphase DNA FISH: The metaphase DNA FISH protocol was developed using the methods from Beliveau, B. J., et al. (PNAS. 115, 2183-2192 (2018)), Kishi, J. Y., et al. (bioRxiv. (2018)), and Beliveau, B. J., et al. (PNAS. 109, 21301-21306 (2012)). Human metaphase chromosome spreads (XX 46N or XY 46N, Applied Genetics Laboratories) were denatured in 2×SSC+0.1% (vol/vol) Tween-20 (SSCT)+70% (vol/vol) formamide at 70° C. for 90 seconds before being immediately transferred to ice-cold 70% (vol/vol) ethanol for 5 minutes. Samples were then immersed in ice-cold 90% (vol/vol) ethanol for 5 minutes and then transferred to ice-cold 100% ethanol for a further 5 minutes. Slides were then air-dried before 25 μL of ISH solution comprising 2×SSCT, 50% (vol/vol) formamide, 10% (wt/vol) dextran sulfate, 40 ng/μL RNase A (EN0531, Thermo Fisher), and MeRPy-PCR generated probe pool at 1.5 μM final concentration was added. Rubber cement was used to seal the hybridization solution underneath a coverslip, and the sample was placed into a humidified chamber inside an air incubator at 45° C. overnight. After hybridization, samples were washed in 2×SSCT at 60° C. for 15 minutes and then in 2×SSCT at room temperature (2×5 minutes). Samples were then mounted with 12 μL of SlowFade Gold+DAPI (Thermo Fisher S36939) and sealed underneath a coverslip with nail polish before imaging.

Microscopy: Imaging of iterative branching samples was conducted on an inverted Zeiss Axio Observer Z1 using a 100× Plan-Apochromat Oil N.A. 1.40 objective. Samples were illuminated by using Colibri light source using a 365 nm or 555 LED. A filter set composed of a 365 nm clean-up filter (Zeiss G 365), a 395-nm long-pass dichroic mirror (Zeiss FT 395), and a 445/50 nm band-pass emission filter (Zeiss BP 445/50) was used to visualize DAPI staining. A filter set composed of a 545/25-nm excitation filter (Zeiss BP 545/25), a 570 nm long-pass dichroic mirror (Zeiss FT 570), and a 605/70 nm band-pass emission filter (Zeiss BP 605/70) was used to visualize Cy3 signal. Images were acquired by a Hamamatsu Orca-Flash 4.0 v3 sCMOS camera with 6.5 μm pixels, resulting in an effective magnified pixel size of 65 nm.

DNA synthesis and purification: The 42 k library targeting Human Chromosome 8 was ordered from Twist Bioscience and emulsion PCR was performed using the methods from Beliveau, B. J., et al. (PNAS. 115, 2183-2192 (2018)), Kishi, J. Y., et al. (bioRxiv. (2018)), and Beliveau, B. J., et al. (PNAS. 109, 21301-21306 (2012)). This emulsion PCR product was diluted to a final concentration of 1.25 pg/μL for subsequent amplification and ssDNA recovery with the MeRPy-PCR protocol containing a Cy3-labeled reverse primer ordered from Integrated DNA Technologies.

Cas9 directed HDR in human cells with ssDNA: Human Embryonic Kidney (HEK) 293 Ts with a broken GFP expression vector with AAVS1 gRNA targets were obtained from the Church lab that were negative for *mycoplasma* infection. They were expanded using 10% fetal bovine serum (FBS) in high-glucose DMEM with glutamax passaging at a typical rate of 1:100 and maintained at 37° C. with 5% $CO_2$. Transfection was conducted using Lipofectamine 2000 (Thermofisher Catalogue #11668019) using the protocol recommended by the manufacturer with slight modifications outlined below. 24 hours before transfection ~5.0×10$^4$ cells were seeded per well in a 24 well plate along with 0.5 mL of media. A total of 1 μg of plasmid DNA was transfected using 2 μL of Lipofectamine 2000 per well. The DNA content per well contained 700 ng of hCas9 mixed with 200 ng of gRNA expressing plasmid and 100 ng of ssDNA donor (0.76 pmol for 200 bp donor). HDR was measured by percentage of GFP+ through FACS as follows. Three days post-transfection, the cells were harvested using TrypLE and strained before analysis on the BD LSR. Live cell population was gated using SSC and FSC to separate debris and singlets. GFP+ gates were set using a transfected control cell population that did not receive the HDR donor and controls were performed with ssDNA oligo donor transfection alone.

MeRPY-Primer Polymerization

Materials

Acrylamide-labeled single-stranded DNA (Avoid excessive light exposure)
Acrylamide (AA) (40 wt % stock solution, stored light protected at 4° C.)
Sodium acrylate (SA) (20 wt % stock solution, stored light protected at 4° C.)
5×TBE buffer; 500 mM Tris, 500 mM boric acid, 10 mM EDTA, pH 8.2
10×TE buffer, 50 mM Tris, 1 mM EDTA, pH 8.0
5 M NaCl
Tetramethylethylenediamine (TEMED, stored light protected at 4° C.)
Ammonium persulfate (APS, protected from moisture)
Nitrogen gas ($N_2$)
Hypodermic needle
2 mL glass vial with septum cap
Cold methanol (MeOH), stored at −20° C.
$H_2O$
50 mL centrifuge tubes
20 mL disposable syringe Part I: Polymerization Procedure When changing the production scale, it was ensured that the reaction container (glass vial) had the appropriate size: to achieve efficient $N_2$ purging, ¼ to ⅔ of the container volume had to be filled with the reaction solution.

The following reactions were prepared according to the steps listed below:

| Sample | H2O [μL] | TBE, 5x [μL] | Acrydite tagged primer [μL] | Acrylamide (AA), 40% [μL] | Sodium acrylate (SA), 20% [μL] | TEMED, 5% [μL] | APS, 5 wt % [μL] | Total volume [μL] |
|---|---|---|---|---|---|---|---|---|
| TP | 285.25 | 100 | 50 | 62.5 | 1.25 | 0.5 | 0.5 | 500 |
| P | 335.25 | 100 | — | 62.5 | 1.25 | 0.5 | 0.5 | 500 |

*TP = polymer tagged with primer ssDNA (MeRPy-primer);
P = polymer only

The table below shows the final concentrations in the reaction:

| Sample | Final AA concentration [%] | Final SA concentration [%] | Final APS/TEMED concentration [wt %] | Initial concentration of acrydite tagged primer [μM] | Final concentration of acrydite tagged primer [μM] |
|---|---|---|---|---|---|
| TP | 5 | 0.05 | 0.005 | 1,000 | 100 |
| P | 5 | 0.05 | 0.005 | — | — |

*TP = polymer tagged with primer ssDNA (MeRPy-primer); P = polymer only

Steps

1. First $H_2O$, TBE, acrydite tagged primer, AA and SA were mixed, then solution was bubbled for 20 minutes with $N_2$. The septum cap was pierced with the hypodermic needle and the cap was slightly opened for bubbling.
    a) In the meanwhile, fresh 5 wt % stock solutions of TEMED and APS were prepared:
        i) 5% TEMED: 6.5 μL TEMED+93.5 μL $H_2O$
        ii) 5 wt % APS: 25 mg APS+0.5 mL with $H_2O$
2. TEMED was added to the reaction, the vial was swirled, then APS was added while the $N_2$ continued bubbling for 15 minutes.
3. The septum cap was closed tightly (stopped the bubbling) and the sample was left attached to nitrogen overnight.
    a) The sample was highly viscous the next day Note: All samples could be stored at 4° C. and the purification protocol described below could be resumed at a later date.

Part IIa: Purification Procedure (for Tagged Primer—TP)

1. The nitrogen bubbled solution was mixed with 4.5 mL 1×TE
    I. 350 μL 1×TE was added to the vial, which was vortexed for 1-2 minutes.
    II. A 20 mL disposable syringe was filled with air, a needle was attached to the syringe and the needle was bent to a ~90° angle, using the needle cover.
    III. The vial was turned upside down above a 50 mL centrifuge tube. Then the syringe was used to push air into the bottom of the vial, so that the viscous solution was pushed out and dripped into the centrifuge tube.
    IV. 0.5 mL 1×TE buffer was added to the emptied vial, which was vortexed for 30 seconds, then step III was repeated.
    V. Step IV was repeated 3 times.
    VI. Another 2.15 mL 1×TE buffer was added to the centrifuge tube to get to a total volume of 4.5 mL of added 1×TE buffer.
2. Vortexing or shaking was conducted at high speed for 10 minutes.
3. 25 μL 5 M NaCl was added and vortexing was conducted for a few seconds
4. A 50 μL aliquot was taken out for analysis later (UP)
5. Using a syringe: Filled up with 5 mL cold MeOH. Note: the centrifuge cap was removed and vortexing was conducted on low speed, in order to avoid spillage.
    a) 5 mL was slowly added, while vortexing. The last 1-2 mL of MeOH turned the clear liquid turbid, forming a precipitate.
6. The sample was incubated for 2 minutes on ice.
7. The sample was centrifuged at 150 g at 4° C. for 5 minutes and the supernatant was decanted.
    a) 100 μL of supernatant was kept for later analysis (SN1)
8. Re-precipitate:
    a) The pellet was resuspended by adding 4.5 mL with $H_2O$, vortexed for 10 minutes, then 0.5 mL 10×TE buffer and 30 μL 5 M NaCl were added.
    b) Using a syringe: Filled up with 5 mL cold MeOH.
        i) 5 mL was slowly added, while vortexing. The last 1-2 mL of MeOH turned the clear liquid turbid, forming a precipitate.
    c) The sample was spun down at 150 g for 5 minutes and the supernatant was decanted.
    d) 100 μL of supernatant was kept for later analysis (SN2)
9. 4.5 mL $H_2O$ was added to the pellet and vortexing was conducted for 10 minutes, ensuring the pellet was perfectly dispersed 10. 0.5 mL 10×TE buffer was added and vortexed shortly
11. The resuspension was divided into aliquots, which were stored in a −20° C. freezer (TP).

Part IIb: Purification Procedure (for Polymer without Primer—P)

For this procedure, steps 1 to 8 were identical to Part IIa. Note: the unpurified polymer reaction (UP) and the supernatants 1 (SN1) and 2 (SN2) were not needed for analysis, since there was no DNA present in this sample.

9. 5 mL $H_2O$ was added to the pellet and vortexing was conducted for 10 minutes, ensuring the pellet was perfectly dispersed.
10. The resuspension was divided into aliquots, which were stored in a −20° C. freezer.

General PCT Setup

Herein, the generalized PCR mixes and thermocycler protocols for standard Taq polymerase are reported as well as Phusion high-fidelity PCR master mix with HF buffer, as these two polymerases generated all the ssDNA needed to carry out the disclosed experiments. This strand purification protocol was successfully performed from PCRs of different polymerases (Hot Start Taq DNA Polymerase and Kapa Taq), highlighting the generalizability of this recovery method. The results for other polymerases are not reported here as the ssDNA generated was not a part of any downstream application or figure reported herein.

Standard Taq Polymerase PCR Setup

All PCRs using standard Taq polymerase were prepared using this general protocol:

| Component | 100 μL reaction | Final concentration |
| --- | --- | --- |
| Nuclease-free $H_2O$ | Bring volume up to 100 μL | |
| 10× Standard Taq buffer | 10 μL | 1× |
| 10 mM (each) dNTPs | 2 μL | 200 μM |
| 10 uM untagged primer | 2 μL | 0.2 μM |
| X uM MeRPy-primer | Variable* | 0.2 μM |
| 10 nM DNA template | 1 μL | 0.1 nM |
| Standard Taq DNA polymerase | 0.5 μL | 2.5 units/100 μL PCR |

*Amount of MeRPy-primer to use is dependent on stock concentration prepared after polymerization, but the final concentration should be equal to that of the untagged primer.

Standard Taq Polymerase Thermocycler Protocol

| Step | Temperature (° C.) | Time (s) |
| --- | --- | --- |
| Initial denaturing | 95 | 30 |
| Denaturing | 95 | 15 |
| Annealing | Variable* | 15 |
| Extension | 68 | Variable** |
| Cycle | 29 additional cycles | |
| Final extension | 68 | 300 |
| Hold | 4 | forever |

*The annealing temperature depends on the exact primer pair used. Annealing temperatures were calculated based on NEB's Tm calculator's recommended temperature (generally 5° C. below the annealing temperature of the primer with the lower Tm).
**The extension temperature for all lower range amplicons (>500 nt) was 15 seconds, however higher range amplicons followed NEB's recommend extension time of 1 minute per kilobase.

Phusion PCR Setup

| Component | 100 μL reaction | Final concentration |
| --- | --- | --- |
| Nuclease-free $H_2O$ | Bring volume up to 100 μL | |
| 10 uM untagged primer | 5 μL | 0.5 μM |
| X uM MeRPy-primer | Variable* | 0.5 μM |
| 10 nM DNA template | 4 μL | 0.4 nM |
| 2× Phusion master mix | 50 μL | 1× |

*Amount of MeRPy-primer to use depends on stock concentration prepared after polymerization, but the final concentration should be equal to that of the untagged primer.

Phusion Thermocycler Protocol

| Step | Temperature (° C.) | Time (s) |
| --- | --- | --- |
| Initial denaturing | 98 | 30 |
| Denaturing | 98 | 10 |
| Annealing | Variable* | 30 |
| Extension | 72 | Variable** |
| Cycle | X 29-34 additional cycles | |
| Final extension | 72 | 240 |
| Hold | 4 | forever |

*The annealing temperature depends on the exact primer pair used. Annealing temperatures were calculated based on NEB's Tm calculator's recommended temperature (generally at the annealing temperature of the primer with the lower Tm).
**The extension temperature followed NEB's recommend extension time of 15-30 seconds per kb.

Strand Recovery

Materials

1% linear polyacrylamide (without DNA primers) in $H_2O$
Methanol (ice cold)
Basic denaturing buffer (BDB; 0.2 M NaOH, 2 mM EDTA)
Washing solution (1 part 5 mM Tris-1 mM EDTA (pH 8), 30 mM NaCl and 1 part MeOH)
Uracil DNA glycosylase (UDG) and accompanying 10×UDG buffer
10× 1,2-Dimethylethylenediamine (DMEDA; 1, buffered to pH 8-9 with acetic acid)
1 M sodium chloride (NaCl)
Isopropanol
3 M sodium acetate (NaOAc; pH 5.3)
Molecular biology grade glycogen
70-75% ethanol (EtOH)
1× Tris-EDTA (TE)
$H_2O$
1.5-2 mL eppendorf tubes Part I: Strand 1 Recovery (Native and Denaturing Precipitations)

1. ⅓ volume of 1 wt % polymer was added without DNA primers to the PCR sample (i.e. if the initial PCR sample was 300 μL then 100 μL of 1 wt % polymer was added)
   a) Prior to adding polymer, 5-10 μL was saved for quality control (Raw PCR)
2. Native precipitation: 1 volume ice cold methanol (MeOH) was added in to sample and the precipitate was vortexed
3. The precipitate was incubated for at least 1 minute, then centrifuged at 350-2000 g (4° C.) for 5 minutes (FIG. 6)
4. The supernatant was decanted or gently pipetted
   a) The supernatant was saved for quality control as supernatant 1 (SN1)
5. The pellet was resuspended in $H_2O$ up to initial sample volume
   a) 10 μL was saved for quality control as PCR input control for PAGE analysis (Clean PCR)
6. Denaturing step: 0.22 volumes of basic denaturing buffer (BDB; 0.2 M NaOH, 2 mM EDTA; final concentration of 44 mM NaOH) was spiked into the sample a) For shorter length strands (<500 nt), vortexing then 1-minute incubation was conducted
b) For mid-length strands (500-1,000 nt), vortexing then 5-minute incubation was conducted
c) For longer length strands (1,000+nt), vortexing then 10-minute incubation was conducted
7. Denaturing precipitation: 1 volume of MeOH was added, vortexing then 1-minute incubation was conducted
8. Samples were spun at 350-2,000 g (centrifuged at <4° C.) then the supernatant was transferred to a fresh tube (this supernatant contained strand 1)
   a) The supernatant was spun again at 20,000 g (centrifuged at <4° C.) to remove any remaining polymer
   b) 10 μL of supernatant was saved for quality control (SN2)
   c) The supernatant was transferred to a new tube and proceeded to isopropanol precipitation
9. The pellet was washed with 1 volume of washing solution (1 part 1×TRIS-EDTA, 30 mM NaCl and 1 part MeOH)
10. Vortexing was conducted for 5 seconds, then the sample was spun down at 350-2,000 g (4° C.) for 5 minutes
11. The supernatant was decanted or gently pipetted
12. The sample was resuspended in $H_2O$ back up to initial sample volume
13. The sample proceeded to strand 2 recovery Part II: Strand 2 Recovery (UDG/DMEDA Strand Cleavage)
1. The following uracil DNA glycosylase (UDG) reaction was prepared to create abasic sites from deoxyuridine bases:
   a) 1 volume of sample (all of sample from part one of protocol)
   b) 10×UDG buffer
   c) UDG (0.5 μL per 200 μL sample)
   d) $H_2O$ as needed to adjust final volume
2. The sample was incubated at 37° C. for 15 minutes
3. The abasic site was cleaved by spiking in an appropriate amount of 10×DMEDA (1 M; pH 8-9; buffered in acetic acid)
4. The sample was incubated at 37° C. for 15 minutes
5. 0.04 volumes of 1 M NaCl was added to the sample to aid in polymer precipitation following DMEDA treatment
6. 1 volume of MeOH was added to the sample, then it was vortexed and incubated for 1 minute to precipitate
7. The sample was centrifuged at 20,000 g (centrifuged at <4° C.) to remove remaining polymer
8. The supernatant was transferred to a fresh tube and proceeded to isopropanol precipitation
   a) 10 μL of supernatant was saved for quality control (SN3)

Part III: Isopropanol Precipitation
1. The following isopropanol precipitation was set up for both strand 1 and strand 2:
   a) 0.1 volumes 3 M sodium acetate (NaOAc) was added
   b) 0.8 volumes isopropanol (iPrOH) was added
   c) Optional: glycogen was added as a carrier molecule to improve visibility of precipitated ssDNA (5 μL glycogen per 1 mL of sample)
2. The sample was incubated at −20° C. for at least 2 hours (usually 12 hours)
3. The sample was spun at 20,000 g (centrifuged at <4° C.) for 45 minutes and the supernatant was decanted
4. Washing was conducted with 70-75% EtOH
5. The sample was spun for 15 minutes at 20,000 g (centrifuged at <4° C.) and the supernatant was decanted
6. Optional: the wash step was repeated
7. The pellet was air dried at room temperature or 37° C.
8. The pellet was then resuspended in desired volume of 1×TE or any other preferred buffer
9. The samples were nanodropped.

Recovery Yield of Strand 1 and 2

Data shown in FIG. 5 was calculated based on the triplicate MeRPy-PCR results. The nanodrop results (calculated into pmol) from the recovered strands 1 and 2 after iPrOH precipitation were compared to the densitometry analysis (data not shown) of the MeRPy-PCR reaction after the first native precipitation. Amplicons generated with MeRPy-PCR were tagged and unable to migrate into the gel. In order to obtain MeRPy-PCR yields, the samples had to be denatured and separated on denaturing polyacrylamide gel electrophoresis, allowing strand 1 to migrate into the gel. The 3,115 bp MeRPy-PCR amplicon was denatured with formamide and subsequently eluted on a native agarose gel.

Effect of NaOH Denaturation on the Recovery Yield of Strand 2

It was noted that extended exposures of the linear polyacrylamide to the denaturing buffer (NaOH) can cause irreversible polymer damage. Incubation times beyond 10 minutes led to complete destruction of the polymer and its inability to precipitate from solution with MeOH. It was also observed that longer incubations with denaturing buffer led to decreased strand 2 recovery, likely caused by the additional damage to the polymer. Herein, it was hypothesized that this is why there is diminishing strand 2 recovery as the strand length increases; longer strands require longer denaturing incubations and therefore result in lower recovery yields of strand 2. This hypothesis was in accordance with the results in FIG. 5 as there were consistent strand 2 yields for the lower range strands as they all followed the same denaturation protocol. However, a decrease in yield for the mid-length strand and an even further decrease in yield for the longer length strand were observed.

Fluorescence-activated cell sorting (FACS) scatter plots: Live cell population was gated using SSC and FSC to separate debris and singlets. GFP+ gates were set using a transfected control cell population that did not receive the HDR donor and controls were performed with ssDNA oligo donor transfection alone.

TABLE 1

Densitometry analysis results of polymer tagged primer capture yield.

| Sample: | Final concentration (μM): | Capture yield (%) |
| --- | --- | --- |
| TP - polymer tagged primer used in FIG. 5 for all templates | 8.823675359 | 88.23675359 |

TABLE 2

Capture yield for MeRPy-primers used in FIG. 6. Capture yield was determined by nanodrop analysis (preceded blanking with linear polymer of same wt % without DNA handles).

| Sample: | Nucleic Acid | Unit | A260 (Abs) | Concentration (μM) | Capture yield (%) |
|---|---|---|---|---|---|
| Polymer tagged primer for 200mer | 43.2 | ng/μl | 1.308 | 5.850804486 | 58.50804486 |
| Polymer tagged primer for 400mer | 20.2 | ng/μl | 0.613 | 3.647723784 | 36.47723784 |
| Polymer tagged primer for 600mer | 28.4 | ng/μl | 0.86 | 4.61563465 | 46.1563465 |
| Polymer tagged primer for 800mer | 33.7 | ng/μl | 1.021 | 4.979093716 | 49.79093716 |
| Polymer tagged primer for 1000mer | 23.4 | ng/μl | 0.708 | 3.45729356 | 34.5729356 |
| DNA-Origami scaffold polymer tagged primer | 29.5 | ng/μl | 0.89 | 4.16* | 83.2 |
| FISH probes polymer tagged primer | 53.2 | ng/μl | 1.61 | 8.23 | 82.3 |

TABLE 3

Nanodrop results of ssDNA donor oligos used in genome editing in human cells using CRISPR/Cas9.

| Sample ID | Nucleic Acid | Unit | Strand length (nt) | Yield (pmol/100 μL PCR) |
|---|---|---|---|---|
| 200mer | 85.2 | ng/μl | 200 | 34.5 |
| 400mer | 71 | ng/μl | 370 | 15.575 |
| 600mer | 92.8 | ng/μl | 615 | 14.712 |
| 800mer | 137.7 | ng/μl | 805 | 16.782 |
| 1000mer | 110.5 | ng/μl | 975 | 13.425 |

TABLE 4

Folding reaction mixture for 30 nm barrel. The components were mixed together and then annealed over the course of 20 hours (80° C. (10 minutes), 55° C. → 45° C. (18 hours, 1 hour 48 minutes/° C.), 45° C. → 25° C. (1 hours), 4° C. (hold)). Samples were analyzed via agarose gel electrophoresis (0.5 × TBE; 11 mM MgCl$_2$; pre-stained with EtBr; resolved at 60 V for 3 hours). Upon confirmation of successful folding, the samples were analyzed by negative staining transmission electron microscopy.

| Ingredient | 30 nm barrel (μL) | Control μL) |
|---|---|---|
| 50 mM Tris, 10 mM EDTA, pH 8.0 | 3.4 | 0.96 |
| 60 mM MgCl2 | 4 | 1.13 |
| ss-3315 (50 nM) | 5.5 | 1.6 |
| staple + miniscaf stock (500 nM each) | 8 | — |
| water | 19.1 | 7.61 |
| total volume | 40 | 11.3 |

TABLE 5

Nanodrop results of ssDNA scaffold used in DNA origami folding of the 30 nm barrel structure.

| Sample ID | Nucleic Acid | Unit | Strand length (nt) | Yield (pmol/100 μL PCR) |
|---|---|---|---|---|
| ssDNA scaffold for DNA origami | 306.1 | ng/μL | 3315 | 1.35 |

TABLE 6

Nanodrop results of ssDNA probes used in FISH imaging.

| Sample ID | Nucleic Acid | Unit | Strand length (nt) | Yield (pmol/100 μL PCR) |
|---|---|---|---|---|
| FISH library | 281.6 | ng/μl | ~130 | 70.40966 |

REFERENCES

1. Beaucage, S. L., & Caruthers, M. H. Tetrahedron Lett. 20, 1859-1862 (1981).
2. Kujau, M. J., & Wolfl, S. Mol. Biotechnol. 7, 333-335 (1997).
3. Bowman, B. H., & Palumbi, S. R. Methods Enzymol. 224, 399-406 (1993).
4. Schmidt, T. L., et al. Nat. Comm 6, 8634 (2015).
5. Veneziano, R., et al. Sci. Rep. 8, 6548 (2018).
6. Palluk, S., et al. Nat. Biotechnol. 36, 645-650 (2018).
7. Kishi, J. Y., et al. Nat. Chem. 10, 155-164 (2017).
8. Praetorius, F. et al. Nature 552, 84-87 (2017).
9. Krieg, E. & Shih, W. M. Angew. Chem. Int. Ed. Engl. 57, 714-718 (2018).
10. Manuscript in preparation, to be submitted to BioRxiv shortly
11. McHugh, P. J., & Knowland, J. Nucleic Acids Res. 23, 1664-1670 (1995).
12. Rothemund, P. W. Nature 440, 297-302 (2006).
13. Douglas, S. M., et al. Nature 459, 414-418 (2009).
14. Douglas, S. M., et al. Nucleic Acids Res. 37, 5001-5006 (2009).
15. Beliveau, B. J., et al. Proc. Natl. Acad. Sci. USA 109, 21301-21306 (2012).
16. Richardson, C. D., et al. Nat. Biotechnol. 34, 339-344 (2016).
17. Davis, L., & Maizels, N. Cell Rep. 17, 1872-1881 (2016).
18. Roth, T. L., et al. Nature 559, 405-409 (2018).
19. Chen, X., et al. ACS Appl. Mater. Interfaces. 10, 24344-24348 (2018).
20. Ponnuswamy, et al. Nat. Comm 8, 15654 (2017).

What is claimed is:

1. A method for producing single-stranded deoxyribonucleic acid (DNA), the method comprising:
   (a) amplifying, in solution, a DNA template in a polymerase chain reaction mixture that comprises the DNA template, a pair of primers, one of which is tagged with a methanol-responsive polymer (MeRPy) comprising acrylic monomers (a MeRPy-tagged primer) and comprises a cleavage site, a polymerase, and deoxynucleoside triphosphates to produce a double-stranded MeRPy-tagged amplicon; and
   (b) dehybridizing, in solution, the double-stranded MeRPy-tagged amplicon into an untagged DNA strand and a MeRPy-tagged DNA strand comprising the cleavage site, and optionally isolating the untagged DNA strand.

2. The method of claim 1 further comprising cleaving the MeRPy-tagged DNA strand at the cleavage site to produce the MeRPy-tagged primer and single-stranded DNA.

3. The method of claim 2, further comprising isolating the MeRPy-tagged primer and/or the single-stranded DNA.

4. The method of claim 3, wherein isolating the DNA-tagged MeRPy comprises selective precipitation of the DNA-tagged MeRPy or electroelution of the DNA-tagged MeRPy.

5. The method of claim 3, wherein isolating the MeRPy-tagged primer comprises filtration, centrifugation, or selective precipitation of the MeRPy-tagged primer.

6. The method of claim 2, wherein the cleavage site comprises a deoxyuridine (dU), wherein cleaving the MeRPy-tagged DNA strand comprises combining the MeRPy-tagged DNA strand with uracil-DNA glycosylase (UDG) to create an abasic site (AB-site) in the tagged DNA, and cleaving the AB-site with N,N'-Dimethylethylenediamine (DMEDA).

7. The method of claim 2, further comprising folding the untagged DNA strand and/or the single-stranded DNA into a DNA nanostructure.

8. The method of claim 1, wherein the cleavage site is a deoxyuridine (dU).

9. The method of claim 1, wherein the DNA template is a double-strand DNA template or a single-stranded DNA template.

10. The method of claim 1, wherein the MeRPy-tagged primer has a length of 15 to 50 nucleotides.

11. The method of claim 1, wherein the DNA template has a length of 20 to 50,000 nucleotides.

12. The method of claim 1, wherein the single-stranded DNA has a length of 20 to 50,000 nucleotides.

13. The method of claim 1, wherein separating the double-stranded MeRPy-tagged amplicon into an untagged DNA strand and a MeRPy-tagged DNA strand further comprises isolating the untagged DNA strand.

14. The method of claim 13, wherein the yield of the isolated untagged DNA strand is 50% to 100%.

15. The method of claim 1, wherein separating the double-stranded MeRPy-tagged amplicon into an untagged DNA strand and a MeRPy-tagged DNA strand further comprises isolating the MeRPy-tagged DNA strand.

16. The method of claim 15, wherein the yield of the isolated MeRPy-tagged DNA strand is 50% to 100%.

17. The method of claim 1, wherein one of the primers comprises a fluorescent label.

18. The method of claim 1, wherein the untagged DNA strand has a fluorescent label.

19. The method of claim 1, wherein the MeRPy comprises acrylamide monomers.

20. The method of claim 1, further comprising:
   cleaving the MeRPy-tagged DNA strand at the cleavage site to produce the MeRPy-tagged primer and single-stranded DNA,
   wherein the cleavage site comprises a deoxyuridine (dU) and wherein cleaving the MeRPy-tagged DNA strand comprises combining the MeRPy-tagged DNA strand with uracil-DNA glycosylase (UDG) to create an abasic site (AB-site) in the tagged DNA, and cleaving the AB-site with N,N'-Dimethylethylenediamine (DMEDA); and
   isolating the MeRPy-tagged primer and/or the single-stranded DNA, wherein isolating the MeRPy-tagged primer and/or the single-stranded DNA comprises selective precipitation of the MeRPy-tagged primer and/or the single-stranded DNA or electroelution of the MeRPy-tagged primer and/or the single-stranded DNA.

21. A method for producing single-stranded deoxyribonucleic acid (DNA), the method comprising:
   (a) copolymerizing, in solution, a 5'-acrylamide-tagged single-stranded DNA (ssDNA) forward primer with acrylamide monomers to produce a methanol-responsive polymer (MeRPy)-tagged forward primer, wherein the MeRPy comprises acrylamide monomers, wherein the ssDNA forward primer comprises a cleavage site;
   (b) optionally purifying the MeRPy-tagged forward primer;
   (c) amplifying, in solution, a DNA template in a polymerase chain reaction mixture that comprises the DNA template, a pair of primers comprising the MeRPy-tagged forward primer and a reverse primer, a polymerase, and deoxynucleoside triphosphates to produce a double-stranded MeRPy-tagged amplicon; and
   (d) dehybridizing, in solution, the double-stranded MeRPy-tagged amplicon into an untagged DNA strand and a MeRPy-tagged DNA strand comprising the cleavage site, and optionally isolating the untagged DNA strand.

* * * * *